United States Patent [19]

Riefling et al.

[11] Patent Number: 4,733,011
[45] Date of Patent: Mar. 22, 1988

[54] NEW INTERMEDIATES FOR THE PREPARATION OF 13-THIAPROSTAGLANDIN DERIVATIVES

[75] Inventors: Bernhard Riefling, Seeheim; Hans-Eckart Radunz, Mühltal, both of Fed. Rep. of Germany

[73] Assignee: Merck Patent Gesellschaft mit beschrankter Haftung, Darmstadt, Fed. Rep. of Germany

[21] Appl. No.: 767,015

[22] Filed: Aug. 19, 1985

Related U.S. Application Data

[62] Division of Ser. No. 280,191, Jul. 6, 1981, abandoned.

[30] Foreign Application Priority Data

Jul. 4, 1980 [DE] Fed. Rep. of Germany ....... 3025325

[51] Int. Cl.⁴ ............................................. C07C 177/00
[52] U.S. Cl. ...................... 568/43; 546/340; 549/78
[58] Field of Search ................. 568/43; 546/340; 549/78

[56] References Cited

U.S. PATENT DOCUMENTS 4,272,629 6/1981 Roberts ................................. 549/11

FOREIGN PATENT DOCUMENTS 1072549 2/1980 Canada ................................. 560/121

OTHER PUBLICATIONS

Morton et al, Adv. Photochem. 1974, 9, 197.

Primary Examiner—Robert Gerstl
Attorney, Agent, or Firm—Millen & White

[57] ABSTRACT

Compounds of the formula

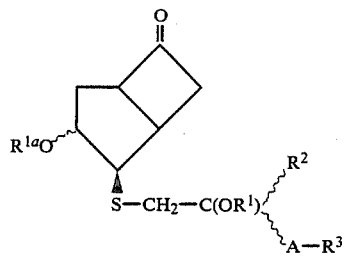

wherein A is C—C single bond, —CH$_2$—, —CH(CH$_3$)—, —C(CH$_3$)$_2$—, —CH$_2$—CH$_2$—, CH(CH$_3$)CH$_2$—, —C(CH$_3$)$_2$CH$_2$—, —CH$_2$—CH$_2$—CH$_2$— or —CH$_2$O—; R$^{1a}$ and R$^1$ each independently is hydrogen or a protective group which can be cleaved by solvolysis or by hydrogenolysis; R$^2$ is H or alkyl of 1 to 3 C atoms; R$^3$ is alkyl of 3 to 5 C atoms, phenyl or phenyl which is monosubstituted to trisubstituted by F, Cl, OH, OCH$_3$, OC$_2$H$_5$, CF$_3$ or alkyl of 1 to 3 C atoms, or, when A is not —CH$_2$O—, can also be pyridyl, thienyl, naphthyl or alkoxy of 1 to 4 C atoms; ▬ indicates a bond in the β-position and wavy line (~) means that the bond can be in the α- or β-position, are valuable intermediates for the stereospecific preparation of 13-thiaprostaglandin derivatives. The latter are prepared by U.V. irradiation of the former to first prepare the corresponding 2-oxa-3-OH-6-alkylthio-7-OH-1,5-bicyclo(3.3.0)octane derivative, which is then exposed to a Wittig reaction and, optionally, hydrogenation or oxidation inter alia to prepare members of the F$_1$-, F$_2$-, E$_1$- and E$_2$ series.

17 Claims, No Drawings

NEW INTERMEDIATES FOR THE PREPARATION OF 13-THIAPROSTAGLANDIN DERIVATIVES

This is a division, of application Ser. No. 280,191 filed July 6, 1981 now abandoned.

BACKGROUND OF THE INVENTION

The present invention relates to new 13-thiaprostaglandin intermediates which are exceptionally valuable for the stereospecific preparation of 13-thiaprostaglandin derivatives. It also relates to their preparation and use for the preparation of known 13-thiaprostaglandin derivatives. Moreover, the invention relates to a new process for the preparation of known 13-thiaprostaglandin derivatives, starting from the new intermediates.

13-Thiaprostaglandin derivatives are known from German Offenlegungsschrift Nos. 2,256,537, 2,422,924 and U.S. Ser. No. 096,348, filed on Nov. 21, 1979, corresponding to German Offenlegungsschrift No. 2,644,972, and possess valuable pharmacological properties. In this regard, the disclosures of all of these references are incorporated by reference herein. These 13-thiaprostaglandin derivatives, for example, in particular those of the E type, have a hypotensive action. This action is evident, for example, on administration, by continuous infusion, to cats narcotized with barbiturate. In this test, the arterial blood pressure is recorded kymographically. The test substances are infused in aqueous propylene glycol solution over a period of 10 minutes.

Moreover, the 13-thiaprostaglandin derivatives have vasodilative, antiphlogistic, diuretic and bronchial spasm-relieving properties; inhibitory effects on the secretion of gastric juice, the aggregation of thrombocytes, the degradation of lipids and the release of noradrenalin; and also nasal decongestant properties. These can likewise be established by fully conventional methods.

The 13-thiaprostaglandin derivatives can also influence the function of the corpus luteum, the transfer of ova through the fallopian tubes, nidation and fertility. Thus, these 13-thiaprostaglandin derivatives, in particular those of the F type, show an oestrus-synchronizing action, for example in cattle, horses, sheep, pigs and dogs. In order to utilize this action, the active compound is injected intramuscularly, advantageously between the 7th day and the 12th day of the cycle.

Several processes for the preparation of these 13-thiaprostaglandin derivatives are known, but they have certain disadvantages. The yields are not always satisfactory, the syntheses proceed via a large number of reaction steps, the work-up is difficult and the purity of the resulting products leaves something to be desired. In particular, in synthesizing these 13-thiaprostaglandin derivatives, which is difficult because of the complex stereochemistry involved, there is a need for processes which lead to isomerically and epimerically pure products in a few reaction steps.

SUMMARY OF THE INVENTION

Accordingly, it is an object of this invention to provide new compounds which, as a result of their regiospecificity and stability, are suitable as starting materials for the preparation of 13-thiaprostaglandin derivatives.

A further object of this invention is to provide a new process for the preparation of 13-thiaprostaglandin derivatives, starting from these new compounds, which process does not possess the disadvantages of the known processes or possesses these disadvantages to a lesser extent.

Upon further study of the specification and appended claims, further objects and advantages of this invention will become apparent to those skilled in the art.

These objects have been achieved by the preparation of the new 13-thiaprostaglandin intermediates of this invention.

In one aspect, this invention thus relates to compounds of formula I

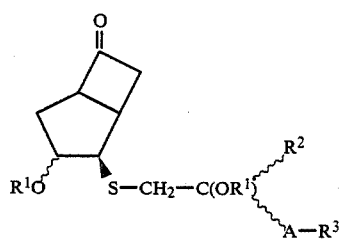

wherein A is a C—C single bond, —$CH_2$—, —CH(CH$_3$)—, —C(CH$_3$)$_2$—, —$CH_2$—$CH_2$—, CH(CH$_3$)CH$_2$—, —C(CH$_3$)$_2$CH$_2$—, —$CH_2$—$CH_2$—$CH_2$— or —CH$_2$O—; $R^1$ is hydrogen or a protective group which can be cleaved by solvolysis or hydrogenolysis; $R^2$ is H or alkyl of 1 to 3 C atoms; $R^3$ is alkyl of 3 to 5 C atoms, phenyl, phenyl which is monosubstituted to trisubstituted by F, Cl, OH, OCH$_3$, OC$_2$H$_5$, CF$_3$ or alkyl of 1 to 3 C atoms, or, when A is not —CH$_2$O—, also pyridyl, thienyl, naphthyl or alkoxy of 1 to 4 C atoms; ◂ indicates a bond in the β-position and a wavy line (~) means that the bond can be in the α- or β-position.

The compounds of formula I contain 4 asymmetrical C atoms in the five-membered ring. Further centers of asymmetry can occur in the thioether side-chain. The compounds of formula 1 can therefore occur in a multiplicity of stereoisomeric forms. In addition to the individual racemates and racemic mixtures, the invention also relates to the optically active isomers of formula I.

This invention further relates in another aspect to a process for preparing a compound of formula I, which comprises reacting 2-bromo-3-hydroxy-bicyclo[3.2.0]-heptan-6-one with a thiol or thiolate of formula II

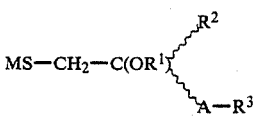

wherein M is H, one equivalent of a metal atom or ammonium and A and $R^1$ to $R^3$ are as defined above, and, if appropriate, blocking one or more available hydroxy groups by a protective group which can be cleaved by solvolysis or hydrogenolysis.

Likewise, the invention relates in yet another aspect to the use of the compounds of formula I for the preparation of 13-thiaprostaglandin derivatives of formula III

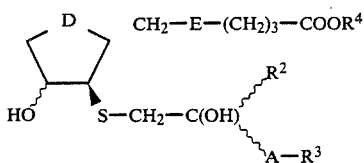

wherein D is —CO— or —CHOH—; E is —CH$_2$—CH$_2$— or —CH=CH—; R$^4$ is H, alkyl of 1 to 4 C atoms or —Q—NH—COR$^5$; Q is 1,4-phenylene or 1,4-naphthylene; R$^5$ is NH$_2$, CH$_3$, phenyl, p-acetylaminophenyl, p-benzoylaminophenyl or phenylamino; A, R$^2$ and R$^3$ are as defined above; and ... indicates a bond in the α-position, ◂ indicates a bond in the β-position and a wavy line (∼) means that these bonds can be in the α- or β-position; and also for the preparation of the physiologically acceptable salts when R$^4$ is hydrogen, by a process comprising, irradiating a compound of formula I with ultraviolet radiation and reacting the resulting lactol of formula IV

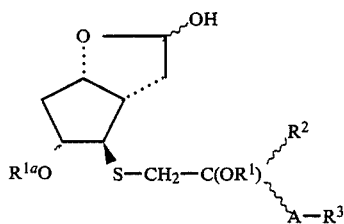

wherein A and R$^1$ to R$^3$ are as defined above, ... indicates a bond in the α-position, ◂ indicates a bond in the β-position and a wavy line (∼) means that these bonds can be in the α- or β-position, with a compound of formula V $$[(R^6)_3P^{(+)}-(CH_2)_4-COOR^4]X^{(-)} \qquad V$$

wherein R$^6$ is alkyl of 1-4 C atoms or phenyl, X is Cl, Br or I and R$^4$ is as defined above; and, if appropriate, converting a compound of formula III in which E=—CH=CH— by hydrogenation into a compound of formula III in which E=—CH$_2$—CH$_2$—; and/or cleaving by solvolysis or hydrogenolysis available protective groups in the C$_{11}$— and C$_{15}$—positions; and/or, in order to prepare the 13-thiaprostaglandin E-analog of formula III, selectively blocking the hydroxyl groups in the C$_{11}$- and C$_{15}$-positions, at any desired stage, by protective groups which can be cleaved by solvolysis or hydrogenolysis, oxidizing the free hydroxyl group in the C$_9$-position to a keto group and cleaving by solvolysis or hydrogenolysis the protective groups in the C$_{11}$- and C$_{15}$-positions; and/or, if appropriate, converting a compound of formula III in which R$^4$=H, by reaction with a corresponding esterifying agent, into another compound of formula III in which R$^4$=alkyl of 1 to 4 C atoms; and/or, if appropriate, converting a compound of formula III in which R$^4$=H, by reaction with a compound of formula VI $$HO\text{-}Q\text{-}NH\text{-}COR^5 \qquad VI$$

into another compound of the formula III in which R$^4$=—Q—NH—COR$^5$; and/or, if appropriate, converting a compound of formula III in which R$^4$=alkyl of 1-4 C atoms or —Q—NH—COR$^5$, by reaction with a solvolyzing agent, into another compound of formula III in which R$^4$=H; and/or, if appropriate, splitting a compound of formula III into its racemates and/or enantiomers; and/or, if appropriate, converting a compound of formula III in which R$^4$=H by treatment with a base, into one of its physiologically acceptable salts or liberating it from one of its salts by treatment with an acid.

DETAILED DISCUSSION

The compounds of formula I are valuable intermediates in the stereospecific synthesis of 13-thiaprostaglandin derivatives. Because the side-chain containing the sulfur atom is introduced in an early step of the synthesis, troublesome isomers and epimers can be separated off at an initial stage. Consequently, the desired 13-thiaprostaglandin derivative is obtained isomerically and epimerically pure in the last step. Indeed, it must be regarded as surprising and unforeseeable that the reaction of a thiol of formula II with 2-bromo-3-hydroxy-bicyclo-[3.2.0]-heptan-6-one leads almost exclusively to the desired compounds of formula I, in an extremely regiospecific reaction. The undesired isomer is formed only in trace amounts and can moreover be separated off easily by recrystallization.

A similar regiospecific reaction, namely the reaction of 2,3-epoxy-bicyclo[3.2.0]heptan-6-one, or derivatives of this compound, with an organometallic reagent containing 1 to 12 C atoms, is in fact known from German Offenlegungsschrift No. 2,800,929; however, there are no indications at all that the reaction of this invention, namely that of 2-bromo-3-hydroxy-bicyclo[3.2.0]heptan-6-one with a thiol or a thiolate, produces the desired compounds in this extremely regiospecific manner. Furthermore, the reaction of this invention can be carried out in the simplest manner at room temperature, while for the reaction described in German Offenlegungsschrift No. 2,800,929, special procedures must be observed.

Also, the new process for the preparation of the 13-thiaprostaglandin derivatives of formula III, which is based on the new compounds of formula I as starting materials, possesses decisive advantages compared with various known processes.

The ultraviolet irradiation of a compound of formula I produces the lactols of formula IV under mild conditions, 11α,15at room temperature, and avoids dangerous and expensive reagents. On the other hand, the process known hitherto (compare Corey et al, Tetrahedron Letters, 311, 1970) involves the reduction of a lactone in which the expensive and dangerous diisobutyl-aluminum hydride is employed at low temperature.

The reaction of cyclobutanones to give cyclic acetals by ultraviolet irradiation in alcoholic solutions has already been exhaustively investigated (Yates et al, Tetrahedron Letters, 1964, 1,739; Yates et al, Accounts Chem. Res. 1975, 8, 209; and Turro et al, Adv. Photochem., 1974, 9, 197 ). Also, the reaction of 2,3-epoxy-bicyclo[3.2.0]heptan-6-one to give 2-oxa-3-methoxy-6,7-epoxy-bicyclo[3.3.0]octane by UV irradiation is already known (Crossland et al, J.C.S. Chem. Comm. 1978, 661). However, even in view of these disclosures, it must be regarded as surprising that this reaction can also be carried out with such outstanding results in the case of the present compounds, which contain a hydroxyalkylthio side-chain.

The subsequent reaction of a compound of formula IV with a Wittig reagent of formula V to give the 13-thiaprostaglandin F-analog of formula III has already been described in German Offenlegungsschrift No. 2,550,004, whose disclosures are incorporated by reference herein.

The compounds of formula III are structurally related to the prostaglandins, which are derived from 7-(2-octyl-cyclopentyl)-heptanoic acid (prostanoic acid). The compounds of formula III can therefore be designated as derivatives of 13-thiaprostanoic acid.

In the above formulae, $R^1$ and $R^{1a}$ are hydrogen or a protective group which can be cleaved by solvolysis or hydrogenolysis. Preferably, these protective groups include, for example, saturated or unsaturated, aliphatic, cycloaliphatic or aromatic, substituted or unsubstituted carboxylic or sulfonic acid radicals, i.e., acyl groups, such as hydrocarbon such radicals, or also inorganic acid radicals. Preferred carboxylic acid radicals are derived from fatty acids having 1 to 18, preferably 1 to 6, C atoms, such as formic, acetic, butyric or isobutyric acid, but also, for example, pivalic, trichloroacetic, benzoic, p-nitrobenzoic, palmitic, stearic or oleic acid. Preferred sulfonic acid radicals are derived from alkylsulfonic acids having 1 to 6 C atoms, for example, methanesulfonic or ethanesulfonic acid, or arylsulfonic acids having 6 to 10 C atoms, for example benzene-, p-toluene- or 1- and 2-naphthalene-sulfonic acid, and also from substituted sulfonic acids, such as 2-hydroxyethanesulfonic or 4-bromobenzenesulfonic acid. Preferred inorganic acids are sulfuric acid and phosphoric acid.

Furthermore, the protective groups can also be ether radicals, so that the hydroxyl groups are present in etherified form, for example, aralkoxy preferably having 7 to 19 C atoms, such as benzyloxy, p-methylbenzyloxy, 1- and 2-phenylethoxy, diphenylmethoxy, triphenylmethoxy or 1- or 2-naphthylmethoxy; alkoxy preferably having up to 6 C atoms, especially tert- butoxy; tetrahydropyranyloxy; or tri-$C_{1-4}$-alkylsilyloxy, preferably trimethylsilyloxy or tert - butyldimethylsilyloxy.

Because these protective groups are no longer present in the pharmacologically active compounds of formula III, their nature is not in itself critical.

In addition to hydrogen, $R^2$ is also alkyl having 1-3 C atoms, which is preferably unbranched, such as methyl, ethyl or propyl, but can also be branched, such as isopropyl.

$R^3$ is alkyl of 3-5 C atoms, preferably an unbranched alkyl radical of 3-5 C atoms, such as propyl, butyl, or pentyl; other alkyl radicals $R^3$ include: isopropyl, isobutyl, isopentyl, sec - butyl, tert-butyl, pent-2-yl, pent-3-yl, 2-methylbutyl or neopentyl.

$R^3$ is also preferably phenyl or phenyl which is mono-, di- or tri-substituted by F, Cl, OH, $OCH_3$, $OC_2H_5$, $CF_3$ or alkyl of 1-3 C atoms. If $R^3$ is a substituted phenyl radical, it is preferably monosubstituted, the substituent being located in the 2-position or especially in the 3- or 4-position.

$R^3$ is therefore preferably also 3-fluorophenyl, 4-fluorophenyl, 3-chlorophenyl, 4-chlorophenyl, 3-hydroxyphenyl, 4-hydroxyphenyl, 3-methoxyphenyl, 4-methoxyphenyl, 3-ethoxyphenyl, 4-ethoxyphenyl, 3-trifluoromethylphenyl, 4-trifluoromethylphenyl, 2-tolyl, 3-tolyl, 4-tolyl, 4-ethylphenyl or 4-isopropylphenyl, but also, for example, 2,4-dichloro-, 3,4-dichloro-, 2,4-dimethyl-, 3,4-dimethyl-, 2,4-dimethoxy-, 2,3-dimethoxy-, 2,4,6-trimethyl- or 3,4,5-trimethoxyphenyl.

If A is not $-CH_2O-$, $R^3$ is also methoxy, ethoxy, propoxy or butoxy, 2-pyridyl, 3-pyridyl, 4-pyridyl, 2thienyl, 3-thienyl, 1-naphthyl or 2-naphthyl.

A is preferably $-CH_2-$, $-CH_2-CH_2-$ or $-CH_2O-$. In addition, however, A is also $-CH(CH_3)-$, $-C(CH_3)_2-$, $-CH(CH_3)-CH_2-$, $-C(CH_3)_2CH_2-$ or $-CH_2-CH_2-CH_2-$.

M is preferably H, Na, K, ½ Ca or $NH_4$. In addition, M can also be one equivalent of another metal atom, preferably an alkali metal atom or alkaline earth metal atom, or an ammonium ion substituted by 1-4 alkyl radicals preferably having 1-6 C atoms, by cycloalkyl radicals preferably having 5-7 C atoms or by aralkyl radicals preferably having 7-11 C atoms.

If D is a $-CHOH$ group, the OH group can be in the α- or β-position.

If E is a 1,2-vinylene radical, this is preferably cis-substituted.

$R^4$ is especially hydrogen, but also alkyl, preferably unbranched alkyl having up to 4 C atoms, such as methyl, ethyl, propyl or n-butyl, but it can also be a branched radical, such as isopropyl or tert-butyl. Particularly advantageously, $R^4$ is also the radical $-Q-NH-COR^5$.

Q is preferably 1,4-phenylene, but can also be 1,4-naphthylene.

$R^5$ is preferably methyl, $NH_2$, 4-acetylaminophenyl and especially phenyl.

$R^6$ is alkyl of 1-4 C atoms, preferably an unbranched alkyl radical, such as methyl, ethyl, propyl or butyl, but it can also be branched alkyl having 1-4 C atoms, such as isopropyl, sec-butyl, isobutyl or tert-butyl; in particular however, $R^6$ is phenyl. As a rule, all three radicals $R^6$ are identical, but they can also be different. If $R^6$ is branched alkyl, not more than 2 branched radicals, advantageously only 1 branched alkyl radical, should be linked to the P atom. X is Cl, Br or I, Br being preferred.

Particularly preferred compounds of formula I are those in which at least one of the symbols A, $R^1$, $R^2$ and $R^3$ has one of the meanings indicated above as preferred. Some of these preferred groups of compounds can be characterized by the following partial formulae Ia to Ie, which otherwise correspond to formula I and in which the symbols which have not been indicated in greater detail have the meanings indicated for formula I, but wherein in Ia: $A=-CH_2-$, $-CH(CH_3)-$ or $-C(CH_3)_2-$ and $R^3$=butyl; in Ib: $A=-CH_2-$, $-CH(CH_3)-$ or $-C(CH_3)_2-$, $R^2$=methyl and $R^3$=butyl, in Ic: $A=-CH_2-CH_2-$ or $-CH_2O-$ and $R^3$=phenyl, 3-chlorophenyl, 3-trifluoromethylphenyl or 3-methoxyphenyl; in Id: $A=-CH_2-CH_2-$ or $-CH_2O-$, $R^2$=H or methyl and $R^3$=phenyl, 3-chlorophenyl, 3-trifluoromethylphenyl or 3-methoxyphenyl; and in Ie: $A=-CH_2CH_2-$ or $-CH_2O-$, $R^1$=H, $R^2$=H or methyl and $R^3$=phenyl, 3-chlorophenyl, 3-trifluoromethylphenyl or 3-methoxyphenyl.

2-Bromo-3-hydroxy-bicyclo[3.2.0]heptan-6-one, which is obtained from cyclopentadiene, is described, for example, in J.C.S. Chem. Comm. 1974, page 948.

In the compounds of formula II, the radicals A, $R^2$ and $R^3$ are as defined above, especially those mentioned as preferred. Such compounds of formula II are 2-hydroxythiols or their alkali metal, alkaline earth metal or ammonium salts. Most of the thiols of formula II are known, for example, from German Offenlegungsschrift Nos. 2,256,537, 2,422,924, 2,644,972, whose disclosures are incorporated by reference herein. New compounds of formula II can be prepared from known compounds analogously to known processes, for example, from the corresponding oxiranes by reaction with $H_2S$ and, if appropriate, subsequent conversion into their alkali metal, alkaline earth metal or ammonium salts. Likewise, the oxiranes can be reacted directly with alkali metal, alkaline earth metal or ammonium bisulfides, the compounds of formula II in which M is different from H then being obtained directly.

As a rule, the reaction of 2-bromo-3-hydroxy-bicyclo[3.2.0]heptan-6-one with a thiol or thiolate of formula II is carried out in the presence of a basic catalyst and in the presence or absence of an inert solvent, at temperatures of about $-20°$ to $+100°$, preferably of $0°$ to $30°$. Suitable solvents are preferably alcohols, such as methanol, ethanol, propanol, isopropanol, butanol, tert-butyl alcohol, amyl alcohol, 2-methoxyethanol or 2-ethoxyethanol; ethers, such as diethyl ether, tetrahydrofuran (THF), dioxane or ethylene glycol dimethyl ether; hydrocarbons, such as benzene or toluene; halogenated hydrocarbons, such as methylene chloride or chloroform, or also water.

Examples of suitable basic catalysts include alkali metal or alkaline earth metal hydroxides, such as NaOH, KOH, $Ca(OH)_2$; alkali metal alcoholates, such as $NaOCH_3$, $NaOC_2H_5$ or $KO-tert-C_4H_9$; basic salts, preferably carbonates or acetates, such as $K_2CO_3$ or $NaOCOCH_3$; ammonia; amines, preferably secondary or tertiary amines, such as triethylamine, diisopropylamine, dicyclohexylamine, dimethylaniline, piperidine, 2,6-dimethylpiperidine, 2,2,6,6-tetramethylpiperidine, pyrrolidine, pyridine, quinoline, diazabicyclo[2,2,2]octane or diazabicyclo[3,4,0]nonene, but also primary amines, such as tert-butylamine or cyclohexylamine; or quarternary ammonium hydroxides, such as tetramethylammonium hydroxide or benzyltrimethylammonium hydroxide. It is particularly advantageous to use one of the mentioned amines, especially a secondary or tertiary amine, simultaneously as the solvent and thus to carry out the reaction in the absence of an inert solvent.

The introduction of a protective group which can be cleaved by solvolysis or hydrogenolysis can be carried out by reacting a compound of formula I in which $R^1=H$ with an esterifying or etherifying agent. Examples of esterifying agents are the previously mentioned carboxylic, sulfonic or inorganic acids; examples of etherifying agents are the previously mentioned aromatic alcohols having 7 to 19 C atoms, aliphatic alcohols having up to 6 C atoms, tetrahydropyran and trialkylsilanes.

The introduction of a protective group of this type is advantageously carried out in an inert, preferably anhydrous solvent, for example in an ether, such as diethyl ether or THF, in an alcohol, preferably having up to 4 C atoms, or also in a hydrocarbon, such as petroleum ether, hexane, benzene or toluene, or in mixtures of these solvents, preferably in the presence of an inorganic or organic acid, such as HCl, HBr, HI, $H_2SO_4$, $H_3PO_4$, trifluoroacetic acid, a sulfonic acid, such as benzenesulfonic acid or p-toluenesulfonic acid, or an acid ion exchanger, at temperatures of $-10°$ to $40°$, preferably at room temperature. The reaction times are as a rule 30 minutes to 20 hours.

The compounds of the formula I are valuable intermediates for the preparation of 13-thiaprostaglandin derivatives of formula III.

In the scope of this synthesis, the compounds of the formula I are irradiated with ultraviolet light, preferably of wavelength $\lambda=280-350$ nm. This ultraviolet irradiation is carried out as a rule in aqueous or organic solution, at temperatures of $0°$ to $50°$, preferably of $10°$ to $30°$. The irradiation can be carried out with the aid of the most diverse commercial ultraviolet apparatuses. As a rule, irradiation is carried out with a medium-pressure mercury vapor lamp through a pyrex filter. The irradiation time is generally from 2 to 100 hours, preferably 5 to 50 hours, especially 10 to 20 hours. Solvents which are advantageously used are water or alcohols of 1-5 C atoms, such as methanol, ethanol, propanol, isopropanol, butanol, tert-butyl alcohol or amyl alcohol, or also mixtures of alcohols with water, with esters, such as ethyl acetate, with ketones, such as acetone, with amides, such as DMF, or with hydrocarbons, such as benzene or toluene. It is recommended to add small amounts of butadiene derivatives, such as 2,5-dimethyl-2,4-hexadiene or 1,4-di-tert-butyl-1,3-butadiene, to the reaction mixture. If the ultraviolet irradiation is carried out in alcoholic solution, hydrolysis must subsequently be carried out in the presence of an acid catalyst. The hydrolysis times are about one hour to about 48 hours; the reaction is carried out at temperatures of about $-5°$ to $80°$, preferably at room temperature. Hydrolyzing agents which are preferably used are water or water mixed with organic solvents. Organic solvents which can be used are alcohols, such as methanol, ethanol, propanol, isopropanol, butanol, tert-butyl alcohol, amyl alcohol, 2-methoxyethanol or 2-ethoxyethanol; ethers, such as diethyl ether, THF, dioxane or 1,2-dimethoxyethane; acids, such as formic acid, acetic acid, propionic acid or butyric acid; esters, such as ethyl acetate or butyl acetate; ketones, such as acetone; amides, such as dimethylformamide (DMF) or hexamethylphosphoric acid triamide (HMPT); nitriles, such as acetonitrile; sulfoxides, such as dimethylsulfoxide (DMSO); or sulfones, such as tetrahydrothiophene-S,S-dioxide.

Suitable acid catalysts are inorganic acids, for example hydrochloric, sulfuric, phosphoric, or hydrobromic acid; organic acids, such as chloroacetic acid, trichloroacetic acid or trifluoroacetic acid or methane-, ethane-, benzene- or p-toluene-sulfonic acid, or acidic inorganic salts, such as $MgSO_4$, $Al_2(SO_4)_3$ or $CaCl_2$.

The resulting lactols of formula IV can subsequently be reacted with the compounds of formula V to give the 13-thiaprostaglandin F-analog of formula III. The compounds of formula V are known, for example, from German Offenlegungsschrift No. 2,431,930 and German Offenlegungsschrift No. 2,644,972 and from Tetrahedron Letters 1970, No. 4, pages 311-313, all of whose disclosures are are incorporated by reference herein.

The reaction of a lactol of formula IV with a compound of formula V is known, for example, from German Offenlegungsschrift, No. 2,550,004 and German Offenlegungsschrift No. 2,644,972, whose disclosures are incorporated by reference herein. It is advantageously carried out in an inert organic solvent. Hydrocarbons, such as cyclohexane, toluene, xylene and especially benzene, and also acetonitrile, are preferred; however, ethers, such as diethyl ether, diisopropyl ether, 1,2-dimethoxyethane or THF, for example, are also suitable reaction media. The reaction temperatures are approximately −40° to 150°; the reaction is preferably carried out at room temperature.

The reaction of a compound of formula IV with a compound of formula V can be carried out analogously to the preparation of known compounds, such as PGF$_{2\alpha}$ or 2,3-trans-methano-11,15-bis-tetrahydropyranyl-prostaglandin F$_{2\alpha}$, by standard methods known in the literature, for example described in German Offenlegungsschrift No. 2,431,930, whose disclosure is incorporated by reference herein, for example, by means of a Wittig reaction (which is carried out in the presence of a strong base, for example, an alkali metal hydride, such as NaH, or a lithium-alkyl compound, such as butyllithium), preferably in dimethylsulfoxide (DMSO) as the solvent, at temperatures of about 15° to about 80°. It is particularly advantageous to carry out the reaction under an inert gas atmosphere, for example, under nitrogen. In the compounds of formula I thus obtained, E is a cis C=C double bond.

A compound of the formula III in which E=—CH=CH—can be converted to the corresponding compounds in which E=—CH$_2$—CH$_2$—by, for example, catalytic hydrogenation. Examples of suitable catalysts for catalytic hydrogenations are noble metal, nickel or cobalt catalysts and also mixed catalysts, such as copper/chromium oxide. Suitable noble metals are primarily platinum and palladium, which can be present on supports (for example on charcoal, calcium carbonate or strontium carbonate), as oxides (for example platinum oxide) or in finely divided form. Nickel catalysts and cobalt catalysts are advantageously employed as Raney metals. The hydrogenation can be advantageously carried out at pressures of about 1 to 200 atmospheres and at temperatures of about −80° to +150°, preferably at room temperature. The hydrogenation is carried out in the presence of an inert solvent, for example an alcohol, such as methanol, ethanol or isopropanol, a carboxylic acid, such as acetic acid, an ester, such as ethyl acetate, an ether, such as tetrahydrofuran or dioxane, or a ketone, such as acetone. It is also possible to use solvent mixtures, for example also mixtures containing water.

If desired, a resulting compound of formula III in which D=—CHOH— can be converted to a compound of the formula III in which D=—CO—. Suitable oxidizing agents which enable a group D=—CHOH—to be converted to another group D=—CO— include, in particular, those which have an oxidizing action in a basic, neutral or also weakly acidic medium. Examples of suitable oxidizing agents include ketones, preferably aliphatic or cycloaliphatic ketones, such as acetone or cyclohexanone, and also quinones, such as 1,4-benzoquinone, in the presence of an aluminum alkoxide, preferably aluminum tri-tert-butoxide or aluminum triisopropoxide (Oppenauer oxidation), sulfoxides, preferably dimethyl sulfoxide, if appropriate in the presence of a further auxiliary, for example of a carbodiimide, such as dicyclohexylcarbodiimide, or of a salt of an organic base, such as pyridinium phosphate, pyridinium sulfate, pyridinium chloride or pyridinium trifluoroacetate (Pfitzner-Moffatt oxidation), N-halogenoamides or N-halogenoimides, preferably N-bromoacetamide, N-bromosuccinimide or N-chlorosuccinimide, if appropriate in the presence of further auxiliaries, such as pyridine, acetone or organic sulfides, such as dimethyl sulfide or thioanisole, chlorine, in the presence of an organic sulfide, for example, thioanisole, and organic hypochlorites, preferably tert-butyl hypochlorite, if appropriate in the presence of a preferably tertiary amine, such as pyridine. Further suitable oxidizing agents include chromium trioxide, in the presence of pyridine (Collins reagent) or in the presence of dilute sulfuric acid (Jones reagent), and noble metal salts or noble metal oxides, such as PdCl$_2$, RuO$_4$ or OsO$_4$. Oxidations of the group D=—CHOH—to —CO— should be carried out under relatively mild reaction conditions. The reaction temperatures are approximately −20° to +60°, preferably −15° to room temperature; the reaction times are generally 30 minutes to 4 hours.

Hydroxyl protective groups which may be present in the C$_{11}$- and/or C$_{15}$-positions can be cleaved by solvolysis or hydrogenolysis. The reaction with solvolyzing agents is carried out, for example, at temperatures of −20° to 40°. As a rule, the reaction is carried out in the presence of an acid catalyst, or preferably a basic catalyst, an inert solvent being used.

The solvolyzing agents are preferably hydrolyzing agents, such as pure water or water mixed with organic solvents, usually in the presence of an acid or basic catalyst. Examples of possible organic solvents are alcohols, such as methanol, ethanol, propanol, isopropanol, butanol, tert-butyl alcohol, amyl alcohol, 2-methoxyethanol or 2-ethoxyethanol; ethers, such as diethyl ether, THF, dioxane or ethylene glycol dimethyl ether; acids, such as formic acid, acetic acid, propionic acid or butyric acid; esters, such as ethyl acetate or butyl acetate; ketones, such as acetone; amides, such as dimethylformamide (DMF) or hexamethylphosphoric acid triamide (HMPT); nitriles, such as acetonitrile; sulfoxides, such as DMSO; sulfones, such as tetrahydrothiophene-S,S-dioxide; and also mixtures of these solvents.

Suitable acid catalysts for a solvolysis are inorganic acids, for example hydrochloric, sulfuric, phosphoric or hydrobromic acid; and organic acids, such as chloroacetic acid, trichloroacetic acid or trifluoroacetic acid or methane-, ethane-, benzene- or p-toluene-sulfonic acid. Basic catalysts used for a solvolysis are advantageously alkali metal or alkaline earth metal hydroxides, such as sodium hydroxide, potassium hydroxide or calcium hydroxide, or basic salts, such as sodium carbonate or potassium carbonate. Organic bases, for example ethyl-, diethyl-, triethyl-, isopropyl-, n-butyl- or tri-n-butyl-amine, ethanolamine, triethanolamine, cyclohexylamine, dimethylaniline, pyrrolidine, piperidine, morpholine, pyridine, $\alpha$-picoline or quinoline, or quaternary ammonium hydroxides, such as, for example, tetramethylammonium hydroxide or benzyltrimethylammonium hydroxide, can also be used as basic catalysts. An excess of the catalyst can also be used in place of a solvent.

The solvolysis times are about one hour to about 48 hours; the reaction is carried out at temperatures of about −5° to about 80°, preferably at about room temperature.

The hydrogenolyzing agent is, in particular, catalytically activated hydrogen.

Hydrogenolytic cleavages of protective groups, for example of benzyl groups, with catalytically activated hydrogen are carried out under reaction conditions which are in themselves known, preferably in the presence of a metal catalyst, such as Raney nickel or Raney cobalt, in particular in the presence of a noble metal catalyst, such as Pt or Pd, if appropriate using a support, such as carbon or CaSO$_4$; it also is possible to use oxide catalysts, for example PtO$_2$. Examples of suitable solvents for carrying out the hydrogenolytic cleavage include alcohols, such as methanol or ethanol, carboxylic acids, such as formic or acetic acid, esters, such as ethyl acetate or ethyl butyrate; ketones, such as acetone, ethers, such as THF, or mixtures of these solvents. The hydrogenolyses are preferably carried out at about room temperature to about 40°.

As ester of formula III ($R^4$=alkyl having 1 to 4 C atoms) can be prepared from an acid of formula I ($R^4$=H) by reaction with an esterifying agent. Examples of esterifying agents include alcohols of up to 4 C atoms, preferably in the presence of an inorganic or organic acid, such as HCl, HBr, HI, $H_2SO_4$, $H_3PO_4$, trifluoroacetic acid, a sulfonic acid, such as benzenesulfonic acid or p-toluenesulfonic acid, or an acid ion exchanger; diazoalkanes of up to 4 C atoms, preferably diazomethane; olefins (for example isobutylene), preferably in the presence of acid catalysts (for example $ZnCl_2$, $BF_3$, $H_2SO_4$, arylsulfonic acid, pyrophosphoric acid, boric acid or oxalic acid); alkyl halides of up to 4 C atoms, preferably bromides, such as ethyl, propyl, isopropyl or butyl bromide, but also the corresponding alkyl chlorides or iodides; alkyl carboxylates or sulfonates, the acid radical being of any type and the alkyl radical containing up to 4 C atoms, preferably methyl, ethyl, propyl, isopropyl, or butyl acetate, formate, methylsulfonate, ethylsulfonate or p-toluenesulfonate; and especially also dialkyl sulfates having up to 4 C atoms, such as dimethyl sulfate or diethyl sulfate.

The esterification is advantageously carried out in an inert, preferably anhydrous solvent, for example in an ether, such as diethyl ether or THF, in an alcohol, preferably one of the alcohols having up to 4 C atoms, or also in a hydrocarbon, such as petroleum ether, hexane, benzene or toluene, or in mixtures of these solvents, at temperatures of $-10°$ to 40°, preferably at room temperature. The reaction times are as a rule 30 minutes to 20 hours.

An ester of formula III ($R^4$=—Q—NH—$COR^5$) can be prepared from an acid of formula III ($R^4$=H) by reaction with a compound of formula VI, HO-Q-NH-$COR^5$ (wherein Q and $R^5$ are as defined above). The compounds of formula VI are known, for example from German Offenlegungsschrift No. 2,453,271 and German Offenlegungsschrift No. 2,644,972, whose disclosures are incorporated by reference herein. They are preferably derivatives of p-aminophenol.

The reaction of an acid of formula III ($R^4$=H) with a compound of the formula VI can be carried out by methods which are in themselves known; the reaction is preferably carried out in the presence of a water-binding agent, for example a carboidiimide, such as dicyclohexylcarbodiimide, and in an inert organic solvent, preferably in an ether, such as diethyl ether, 1,2-dimethoxyethane, tetrahydrofuran (THF) or dioxane, or in a halogenohydrocarbon, such as methylene chloride or 1,2-dichloroethane, or in mixtures of these solvents with DMF. Reaction conditions which are suitable for this reaction are known and are described, for example, in Tetrahedron 21, 3, 531 (1965), or in Tetrahedron Letters 1978, 4, 475, whose disclosures are incorporated by reference herein; the reaction temperatures are, for example, approximately 20° to 100°.

Because the esters of formula III in which $R^4$=—Q—NH—$COR^5$ crystallize well, they can also advantageously be used to purify 13-thiaprostaglandins having a free carboxyl group, which are generally obtained as oils which are difficult to purify. After conversion of these oils into the esters of formula III in which $R^4$=—Q—NH—$COR^5$, which crystallize well, the latter can be recrystallized from conventional solvents, simply and in a manner which is in itself known.

Esters of formula III ($R^4$=alkyl of 1-4 C atoms or —Q—NH—$COR^5$) can be converted to an acid of the formula III ($R^4$=H) by hydrolysis. Basic hydrolysis to give the acids of formula III is preferred.

The reaction is preferably carried out in aqueous media, for example in mixtures of water with alcohols, preferably lower alkanols, such as methanol or ethanol, or with ethers, such as ethylene glycol monomethyl ether, ethylene glycol dimethyl ether, THF or dioxane, at temperatures of 0° to 40°, preferably at room temperature. The reaction times are approximately one hour to 12 hours.

The compounds of formula III are usually obtained as mixtures of various stereoisomeric forms, i.e., generally as mixtures of racemates. Racemates can be isolated from the racemate mixtures and obtained pure, for example by recrystallization of the compounds themselves or of derivatives which crystallize well, but especially with the aid of chromatographic methods; adsorption chromatography or partition chromatography, and also mixed forms, are possible methods.

The racemates can be separated into their optical antipodes by known methods, as indicated in the literature. The method of chemical separation is preferred.

Furthermore, it is, of course, possible to obtain optically active compounds by the methods described, by using starting materials which are already optically active.

The compounds of formula III can be mixed with at least one solid, liquid and/or semi-liquid excipient or auxiliary which is customary in pharmacy. The mixtures of the compounds of formula III with the excipients or auxiliaries which are customary in pharmacy can be used as medicaments in human or veterinary medicine. Possible excipients are those organic or inorganic substances which are suitable for parenteral, enteral (for example oral) or topical administration and which do not react with the compounds of formula III, for example water, vegetable oils, benzyl alcohols, polyethylene glycols, glycerin triacetate, gelatin, lactose, starch, magnesium stearate, talc, vaseline and cholesterol. Tablets, coated tablets, capsules, syrups, juices or drops are suitable for oral administration, suppositories are suitable for rectal use, solutions, preferably oily or aqueous solutions, and also suspensions, emulsions or implants are suitable for parenteral use, and ointments, creams or powders are suitable for topical use.

The compounds of formula III can also be lyophilized and the resulting lyophilizates can be used, for example, to produce injection preparations. The preparations indicated can be sterilized, if appropriate, or auxiliaries, such as lubricants, preservatives, stabilizing agents or wetting agents, emulsifiers, salts for influencing the osmotic pressure, buffer substances, colorants, flavorings and/or aromas, can be added thereto. If desired, they can also contain one or more additional active ingredients, for example one or more vitamins.

The compounds of formula III are preferably administered in a dose of 0.01 to 200 mg per dose unit; the dose depends on the species treated, the form of administration and the purpose of the treatment, and it can therefore be less than or in excess of the values indicated above.

If it is desired, for example, to utilize the oestrus-synchronizing action of the compounds of the formula III, it is particularly advantageous to administer about 0.1 mg to about 30 mg, preferably about 0.5 mg to about 20 mg, especially about 1.5 mg to about 15 mg of the active ingredient, by intramuscular injection, for example to cattle (cows or heifers). It is advantageous to administer the effective dose by a single injection between about the 7th day and about the 12th day of the cycle, but it is also possible to inject partial doses several times and, if appropriate, spread over several days, or to inject the effective dose on each of two different days, for example on the 1st and on the 3rd day. The oestrus can also be synchronized in other useful animals, for example in dogs, horses, sheep and pigs, by administration of a compound of formula III. In this case, the effective dose varies according to the average body weight of the species treated, and can easily be determined by those skilled in the art with the aid of the approximate values indicated above for cattle.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

The IR spectra (IR) have been characterized by indicating the main bands (as a film).

The NMR spectra (NMR) were measured in $CDCl_3$ against tetramethylsilane and have been characterized by indicating the signals in ppm.

EXAMPLE 1

102 g of 3α-hydroxy-2β-bromo-1βH,5βH-bicyclo[3.2.0]heptan-6-one and 209 g of 3-(3-chlorophenoxy)-2-hydroxypropylthiol are dissolved in 500 ml of methanol, and a solution of 60 g of potassium tert-butylate in 200 ml of methanol is added dropwise at room temperature. The mixture is then stirred for a further 5 hours and acidified with 5 ml of acetic acid, and the solvent is distilled off. The residue is partitioned between water and methylene chloride, the organic phase is separated off and dried over $MgSO_4$, the solvent is distilled off and, after filtration through a short silica gel column, 3α-hydroxy-2β-(3-(3-chlorophenoxy)-2-hydroxypropylthio)-1βH,5βH-bicyclo[3.2.0]heptan-6-one is obtained as a colorless oil, which crystallizes from toluene at −30° C.

Yield: 84 g.

IR: 1,600, 1,780, 2,950 and 3,400 cm$^{-1}$.

NMR: 3.6–3.8; 4.4; 6.8–7.4.

Analogously to Example 1, the compounds of formula I mentioned in the following Examples 2 to 30 are obtainable from 3-hydroxy-2β-bromo-1,5-bicyclo[3.2.0]heptan-6-one by reaction with a corresponding thiol of formula II:

| Example | Compound of the formula I |
|---|---|
| 2 | 3-Hydroxy-2β-(3-phenoxy-2-hydroxypropylthio)-1,5-bicyclo-[3.2.0]heptan-6-one, |
| 3 | 3-Hydroxy-2β-(3-(4-fluorophenoxy)-2-hydroxypropylthio)-1,5-bicyclo[3.2.0]heptan-6-one, |
| 4 | 3-Hydroxy-2β-(3-(4-chlorophenoxy)-2-hydroxypropylthio)-1,5-bicyclo-[3.2.0]heptan-6-one, |
| 5 | 3-Hydroxy-2β-(3-(4-bromophenoxy)-2-hydroxypropylthio)-1,5-bicyclo[3.2.0]heptan-6-one, |
| 6 | 3-Hydroxy-2β-(3-(4-hydroxyphenoxy)-2-hydroxypropylthio)-1,5-bicyclo[3.2.0]heptan-6-one, |
| 7 | 3-Hydroxy-2β-(3-(4-methoxyphenoxy)-2-hydroxypropylthio)-1,5-bicyclo[3.2.0]heptan-6-one, |
| 8 | 3-Hydroxy-2β-(3-(4-tolyloxy)-2-hydroxypropylthio)-1,5-bicyclo[3.2.0]heptan-6-one, |
| 9 | 3-Hydroxy-2β-(3-(4-trifluoromethylphenoxy)-2-hydroxypropylthio)-1,5-bicyclo[3.2.0]heptan-6-one, |
| 10 | 3-Hydroxy-2β-(3-(3-methoxyphenoxy)-2-hydroxypropylthio)-1,5-bicyclo[3.2.0]heptan-6-one, |
| 11 | 3-Hydroxy-2β-(3-(3-trifluoromethylphenoxy)-2-hydroxypropylthio)-1,5-bicyclo[3.2.0]heptan-6-one, |
| 12 | 3-Hydroxy-2β-(3-(2,4-dichlorophenoxy)-2-hydroxypropylthio)-1,5-bicyclo[3.2.0]heptan-6-one, |
| 13 | 3-Hydroxy-2β-(3-(2,4-dimethoxyphenoxy)-2-hydroxypropylthio)-1,5-bicyclo[3.2.0]heptan-6-one, |
| 14 | 3-Hydroxy-2β-(3-(2,4,6-trimethylphenoxy)-2-hydroxypropylthio)-1,5-bicyclo[3.2.0]heptan-6-one, |
| 15 | 3-Hydroxy-2β-(3-(3,4,5-trimethoxyphenoxy)-2-hydroxypropylthio)-1,5-bicyclo[3.2.0]heptan-6-one, |
| 16 | 3-Hydroxy-2β-(3-phenoxy-2-hydroxy-2-methylpropylthio)-1,5-bicyclo[3.2.0]heptan-6-one, |
| 17 | 3-Hydroxy-2β-(3-(4-fluorophenoxy)-2-hydroxy-2-methylpropylthio)-1,5-bicyclo[3.2.0]heptan-6-one, |
| 18 | 3-Hydroxy-2β-(3-(4-chlorophenoxy)-2-hydroxy-2-methylpropylthio)-1,5-bicyclo[3.2.0]heptan-6-one, |
| 19 | 3-Hydroxy-2 β-(3-(4-bromophenoxy)-2-hydroxy-2-methylpropylthio)-1,5-bicyclo[3.2.0]heptan-6-one, |
| 20 | 3-Hydroxy 2β-(3-(4-hydroxyphenoxy)-2-hydroxy-2-methylpropylthio)-1,5-bicyclo[3.2.0]heptan-6-one, |
| 21 | 3-Hydroxy-2β-(3-(4-methoxyphenoxy)-2-hydroxy-2-methylpropylthio)-1,5-bicyclo[3.2.0]heptan-6-one, |
| 22 | 3-Hydroxy-2β-(3-(4-tolyloxy)-2-hydroxy-2-methylpropylthio)-1,5-bicyclo[3.2.0.]heptan-6-one, |
| 23 | 3-Hydroxy-2β-(3-(4-trifluoromethylphenoxy)-2-hydroxy-2-methylpropylthio)-1,5-bicyclo[3.2.0]-heptan-6-one, |
| 24 | 3-Hydroxy-2β-(3-(3-chlorophenoxy)-2-hydroxy-2-methylpropylthio)-1,5-bicyclo[3.2.0]heptan-6-one, |
| 25 | 3-Hydroxy 2β-(3-(3-methoxyphenoxy)-2-hydroxy-2-methylpropylthio)-1,5-bicyclo[3.2.0]heptan-6-one, |
| 26 | 3-Hydroxy-2β-(3-(3-trifluoromethylphenoxy)-2-hydroxy-2-methylpropylthio)-1,5-bicyclo[3.2.0]-heptan-6-one, |
| 27 | 3-Hydroxy-2β-(3-(2,4-dichlorophenoxy)-2-hydroxy-2-methylpropylthio)-1,5-bicyclo[3.2.0]heptan-6-one, |
| 28 | 3-Hydroxy-2β-(3-(2,4-dimethoxyphenoxy)-2-hydroxy-2-methylpropylthio)-1,5-bicyclo[3.2.0]heptan-6-one, |
| 29 | 3-Hydroxy-2β-(3-(2,4,6-trimethylphenoxy)-2-hydroxy-2-methylpropylthio)-1,5-bicyclo[3.2.0]-heptan-6-one, |
| 30 | 3-Hydroxy-2β-(3-(3,4,5-trimethoxyphenoxy)-2-hydroxy-2-methylpropylthio)-1,5-bicyclo[3.2.0]-heptan-6-one. |

EXAMPLE 31

100 g of 3α-hydroxy-2β-bromo-1βH,5βH-bicyclo[3.2.0]heptan-6-one and 100 g or 2-hydroxy-2-methyl-heptyl-thiol are introduced into 700 ml of methanol, and a solution of 135 g of potassium tert-butylate in 300 ml of methanol is added dropwise. The mixture is stirred for a further 1 hour and acidified with 5 ml of acetic acid, the solvent is distilled off and the residue is taken up in methylene chloride. The organic phase is washed twice with water and dried over $MgSO_4$ and the solvent is distilled off. The oily residue is treated twice with petroleum ether in order to remove excess thiol, filtration is carried out through a short silica gel column and 3α-hydroxy-2β-(2-hydroxy-2-methylheptylthio)-1βH,5βH-bicyclo[3.2.0]heptan-6-one is obtained.

Yield: 79 g.

IR: 1,780, 2,950 and 3,400 cm$^{-1}$.
NMR: 1.28; 2.8; 3.2; 3.6–3.8; 4.4.

Analogously to Example 31, the compounds of formula I mentioned in the following Examples 32 to 43 are obtainable from 3-hydroxy-2β-bromo-1,5-bicyclo[3.2.0]heptan-6-one by reaction with a correspnoding thiol of formula II:

| Example | Compound of the formula I |
|---|---|
| 32 | 3-Hydroxy-2β-(2-hydroxy-heptylthio)-1,5-bicyclo-[3.2.0]heptan-6-one, |
| 33 | 3-Hydroxy-2β-(2-hydroxy-3-methyl-heptylthio)-1,5-bicyclo[3.2.0]heptan-6-one, |
| 34 | 3-Hydroxy-2β-(2-hydroxy-2,3-dimethyl-heptylthio)-1,5-bicyclo[3.2.0]heptan-6-one, |
| 35 | 3-Hydroxy-2β-(2-hydroxy-3,3-dimethyl-heptylthio)-1,5-bicyclo[3.2.0]heptan-6-one, |
| 36 | 3-Hydroxy-2β-(2-hydroxy-3-ethyl-heptylthio)-1,5-bicyclo[3.2.0]heptan-6-one, |
| 37 | 3-Hydroxy-2β-(2-hydroxy-2-methyl-3-ethyl-heptylthio)-1,5-bicyclo[3.2.0]heptan-6-one, |
| 38 | 3-Hydroxy-2β-(2-hydroxy-4-ethyl-heptylthio)-1,5-bicyclo[3.2.0]heptan-6-one, |
| 39 | 3-Hydroxy-2β-(2-hydroxy-2-methyl-4-ethyl-heptylthio)-1,5-bicyclo[3.2.0]heptan-6-one, |
| 40 | 3-Hydroxy-2β-(2-hydroxy-2-methyl-5-methoxy-pentylthio)-1,5-bicyclo[3.2.0]heptan-6-one, |
| 41 | 3-Hydroxy-2β-(2-hydroxy-2-methyl-4-ethoxy-butylthio)-1,5-bicyclo[3.2.0]heptan-6-one, |
| 42 | 3-Hydroxy-2β-(2-hydroxy-2-methyl-3-propoxy-propylthio)-1,5-bicyclo[3.2.0]heptan-6-one, |
| 43 | 3-Hydroxy-2β-(2-hydroxy-2-methyl-3-butoxy-propylthio)-1,5-bicyclo[3.2.0]heptan-6-one. |

EXAMPLE 44

Analogously to Example 1, 3-hydroxy-2β-bromo-1,5-bicyclo[3.2.0]heptan-6-one is reacted with 2-phenyl-2-hydroxy-propylthiol in the presence of potassium tert-butylate, and 3-hydroxy-2β-(2-phenyl-2-hydroxy-propylthio)-1,5-bicyclo[3.2.0]heptan-6-one is obtained.

Analogously to Example 44, the compounds of formula I mentioned in the following Examples 45 to 73 are obtainable by reacting 3-hydroxy-2β-bromo-1,5-bicyclo[3.2.0]heptan-6-one with a corresponding thiol of formula II:

| Example | Compound of the formula I |
|---|---|
| 45 | 3-Hydroxy-2β-(2-(4-fluorophenyl)-2-hydroxy-propylthio)-1,5-bicyclo[3.2.0]heptan-6-one, |
| 46 | 3-Hydroxy-2β-(2-(4-chlorophenyl)-2-hydroxy-propylthio)-1,5-bicyclo[3.2.0]heptan-6-one, |
| 47 | 3-Hydroxy-2β-(2-(4-bromophenyl)-2-hydroxy-propylthio)-1,5-bicyclo[3.2.0]heptan-6-one, |
| 48 | 3-Hydroxy-2β-(2-(4-hydroxyphenyl)-2-hydroxy-propylthio)-1,5-bicyclo[3.2.0]heptan-6-one, |
| 49 | 3-Hydroxy-2β-(2-(4-methoxyphenyl)-2-hydroxy-propylthio)-1,5-bicyclo[3.2.0]heptan-6-one, |
| 50 | 3-Hydroxy-2β-(2-(4-tolyl)-2-hydroxy-propylthio)-1,5-bicyclo[3.2.0]heptan-6-one, |
| 51 | 3-Hydroxy-2β-(2-(4-trifluoromethylphenyl)-2-hydroxy-propylthio)-1,5-bicyclo[3.2.0]heptan-6-one, |
| 52 | 3-Hydroxy-2β-(2-(3-methoxyphenyl)-2-hydroxy-propylthio)-1,5-bicyclo[3.2.0]heptan-6-one, |
| 53 | 3-Hydroxy-2β-(2-(3-chlorophenyl)-2-hydroxy-propylthio)-1,5-bicyclo[3.2.0]heptan-6-one, |
| 54 | 3-Hydroxy-2β-(2-(3-trifluoromethylphenyl)-2-hydroxy-propylthio)-1,5-bicyclo[3.2.0]heptan-6-one, |
| 55 | 3-Hydroxy-2β-(2-(3,4,5-trimethoxyphenyl)-2-hydroxy-propylthio)-1,5-bicyclo[3.2.0]heptan-6-one, |
| 56 | 3-Hydroxy-2β-(3-phenyl-2-methyl-2-hydroxy-propylthio)-1,5-bicyclo-[3.2.0]heptan-6-one, |

-continued

| Example | Compound of the formula I |
|---|---|
| 57 | 3-Hydroxy-2β-(3-(4-fluorophenyl)-2-methyl-2-hydroxy-propylthio)-1,5-bicyclo[3.2.0]heptan-6-one, |
| 58 | 3-Hydroxy-2β-(3-(4-chlorophenyl)-2-methyl-2-hydroxy-propylthio)-1,5-bicyclo[3.2.0]heptan-6-one, |
| 59 | 3-Hydroxy-2β-(3-(4-bromophenyl)-2-methyl-2-hydroxy-propylthio)-1,5-bicyclo[3.2.0]heptan-6-one, |
| 60 | 3-Hydroxy-2β-(3-(4-methoxyphenyl)-2-methyl-2-hydroxy-propylthio)-1,5-bicyclo[3.2.0]heptan-6-one, |
| 61 | 3-Hydroxy-2β-(3-(4-tolyl)-2-methyl-2-hydroxy-propylthio)-1,5-bicyclo[3.2.0]heptan-6-one, |
| 62 | 3-Hydroxy-2β-(3-(4-trifluoromethylphenyl)-2-methyl-2-hydroxy-propylthio)-1,5-bicyclo[3.2.0]heptan-6-one, |
| 63 | 3-Hydroxy-2β-(3-(3-chlorophenyl)-2-methyl-2-hydroxy-propylthio)-1,5-bicyclo[3.2.0]heptan-6-one, |
| 64 | 3-Hydroxy-2β-(3-(3-trifluoromethylphenyl)-2-methyl-2-hydroxy-propylthio)-1,5-bicyclo[3.2.0]heptan-6-one, |
| 65 | 3-Hydroxy-2β-(4-phenyl-2-hydroxy-butylthio)-1,5-bicyclo[3.2.0]heptan-6-one, |
| 66 | 3-Hydroxy-2β-(4-(3-chlorophenyl)-2-hydroxy-butylthio)-1,5-bicyclo[3.2.0]heptan-6-one, |
| 67 | 3-Hydroxy-2β-(4-(3-trifluoromethylphenyl)-2-hydroxy-butylthio)-1,5-bicyclo[3.2.0]heptan-6-one, |
| 68 | 3-Hydroxy-2β-(4-phenyl-2-methyl-2-hydroxy-butylthio)-1,5-bicyclo[3.2.0]heptan-6-one, |
| 69 | 3-Hydroxy-2β-(4-(3-chlorophenyl)-2-methyl-2-hydroxy-butylthio)-1,5-bicyclo[3.2.0]heptan-6-one, |
| 70 | 3-Hydroxy-2β-(4-(3-trifluoromethylphenyl)-2-methyl-2-hydroxy-butylthio)-1,5-bicyclo[3.2.0]heptan-6-one, |
| 71 | 3-Hydroxy-2β-(2-(2-naphthyl)-2-hydroxy-propylthio)-1,5-bicyclo[3.2.0]heptan-6-one, |
| 72 | 3-Hydroxy-2β-(2-(4-pyridyl)-2-hydroxy-propylthio)-1,5-bicyclo[3.2.0]heptan-6-one, |
| 73 | 3-Hydroxy-2β-(2-(2-thienyl)-2-hydroxy-propylthio)-1,5-bicyclo[3.2.0]heptan-6-one. |

EXAMPLE 74

3.41 g of 3α-hydroxy-2β-(3-(3-chlorophenoxy)-2-hydroxypropylthio)-1βH,5βH-bicyclo[3.2.0]heptan-6-one and 4 g of dihydropyran are dissolved in 10 ml of methyl tert-butyl ether, 0.01 g of anhydrous p-toluenesulfonic acid is added and the solution is stirred for 1 hour. It is then washed with sodium bicarbonate solution and dried over sodium sulfate and the solvent is distilled off on a rotary evaporator. This gives 3.44 g of 3α-tetrahydropyran-2-yl-oxy-2β-(3-(3-chlorophenoxy-2-tetrahydropyran-2-yl-oxy-propylthio)-1βH,5βH-bicyclo[3.2.0]heptan-6-one.

EXAMPLE 75

3.41 g of 3α-hydroxy-2β-(3-(3-chlorophenoxy)-2-hydroxypropylthio)-1βH,5βH-bicyclo[3.2.0]heptan-6-one, together with 0.37 g of dimethylaminopyridine, 4.4 g of triethylamine and 3 g of trimethylsilyl chloride, is dissolved in 20 ml of methylene chloride, under nitrogen, and the solution is stirred for 2 days at room temperature. The precipitate is then filtered off, the filtrate is washed twice with saturated ammonium chloride solution and dried over sodium sulfate, and the solvent is distilled off on a rotary evaporator under a waterpump vacuum. This gives 3.62 g of 3α-trimethylsilyloxy-2β-(3-(3-chlorophenoxy)-2-trimethylsilyloxypropylthio)-1βH,5βH-bicyclo[3.2.0]heptan-6-one.

EXAMPLE 76

20 g of 3α-hydroxy-2β-(3-(3-chlorophenoxy)-2-hydroxy-propylthio)-1βH,5βH-bicyclo[3.2.0]heptan-6-one and 1 g of ammonium acetate are dissolved in 70 ml of methanol, nitrogen is passed through the solution for 30 minutes, 1 ml of 2,5-dimethyl-2,4-hexadiene is added and the mixture is irradiated for 2 days with a Hanau Q 600 medium-pressure mercury vapor lamp through a pyrex filter. The solvent is distilled off on a rotary evaporator, the residue is taken up in ethyl acetate and the solution is washed with 1N hydrochloric acid and with water. After drying over sodium sulfate, the solvent is removed and the residue is dissolved in a mixture of 50 ml of acetonitrile and 25 ml of 0.02N hydrochloric acid. The solution is left to stand for 2 days and rendered alkaline with saturated sodium carbonate solution, the acetonitrile is distilled off on a rotary evaporator and the aqueous residue is extracted twice with ethyl acetate. The organic phases are dried over sodium sulfate, some sodium bicarbonate is added and the solvent is distilled off. The residue is then chromatographed on silica gel and 8.2 g of 2-oxa-3-hydroxy-6β-(3-(3-chlorophenoxy)-2-hydroxy-propylthio)-7α-hydroxy-1βH,5βH-bicyclo[3.3.0]octane is obtained.

IR: 1,600, 1,740, 2,900 and 3,400 cm$^{-1}$.
NRM: 0.9–1.4; 2.0–2.3; 2.8–3.1; 3.9–4.3; 6.7–7.3.

Analogously to Example 76, the compounds of formula IV mentioned in the following Examples 77–150 are obtainable from the compounds of formula I mentioned in Examples 2–75:

| Example | Compound of the formula IV |
|---|---|
| 77 | 2-Oxa-3-hydroxy-6β-(3-phenoxy-2-hydroxy-propylthio)-7-hydroxy-1,5-bicyclo[3.3.0]octane, |
| 78 | 2-Oxa-3-hydroxy-6β-(3-(4-fluorophenoxy)-2-hydroxy-propylthio)-7-hydroxy-1,5-bicyclo[3.3.0]octane, |
| 79 | 2-Oxa-3-hydroxy-6β-(3-(4-chlorophenoxy)-2-hydroxy-propylthio)-7-hydroxy-1,5-bicyclo[3.3.0]octane, |
| 80 | 2-Oxa-3-hydroxy-6β-(3-(4-bromophenoxy)-2-hydroxy-propylthio)-7-hydroxy-1,6-bicyclo[3.3.0]octane, |
| 81 | 2-Oxa-3-hydroxy-6β-(3-(4-hydroxyphenoxy)-2-hydroxy-propylthio)-7-hydroxy-1,6-bicyclo[3.3.0]octane, |
| 82 | 2-Oxa-3-hydroxy-6β-(3-(4-methoxyphenoxy)-2-hydroxy-propylthio)-7-hydroxy-1,6-bicyclo[3.3.0]octane, |
| 83 | 2-Oxa-3-hydroxy-6β-(3-(4-tolyloxy)-2-hydroxy-propylthio)-7-hydroxy-1,6-bicyclo[3.3.0]octane, |
| 84 | 2-Oxa-3-hydroxy-6β-(3-(4-trifluoromethylphenoxy)-2-hydroxy-propylthio)-7-hydroxy-1,6-bicyclo[3.3.0]octane, |
| 85 | 2-Oxa-3-hydroxy-6β-(3-(3-methoxyphnoxy)-2-hydroxy-propylthio)-7-hydroxy-1,5-bicyclo[3.3.0]octane, |
| 86 | 2-Oxa-3-hydroxy-6β-(3-(3-trifluoromethylphenoxy)-2-hydroxy-propylthio)-7-hydroxy-1,5-bicyclo-[3.3.0]octane, |
| 87 | 2-Oxa-3-hydroxy-6β-(3-(2,4-dichlorophenoxy)-2-hydroxy-propylthio)-7-hydroxy-1,5-bicyclo-[3.3.0]-octane, |
| 88 | 2-Oxa-3-hydroxy-6β-(3-(2,4-dimethoxyphenoxy)-2-hydroxy-propylthio)-7-hydroxy-1,5-bicyclo[3.3.0]-octane, |
| 89 | 2-Oxa-3-hydroxy-6β-(3-(2,4,6-trimethylphenoxy)-2-hydroxy-propylthio)-7-hydroxy-1,5-bicyclo-[3.3.0]octane, |
| 90 | 2-Oxa-3-hydroxy-6β-(3-(3,4,5-trimethoxyphenoxy)-2-hydroxy-propylthio)-7-hydroxy-1,5-bicyclo[3.3.0]-octane, |
| 91 | 2-Oxa-3-hydroxy-6β-(3-(3-phenoxy-2-hydroxy-2-methyl-propylthio)-7-hydroxy-1,5-bicyclo-[3.3.0]octane, |
| 92 | 2-Oxa-3-hydroxy-6β-(3-(4-fluorophenoxy)-2-hydroxy-2-methyl-propylthio)-7-hydroxy-1,5-bicyclo-[3.3.0]-octane, |
| 93 | 2-Oxa-3-hydroxy-6β-(3-(4-chlorophenoxy)-2-hydroxy-2-methyl-propylthio)-7-hydroxy-1,5-bicyclo-[3.3.0]octane, |
| 94 | 2-Oxa-3-hydroxy-6β-(3-(4-bromophenoxy)-2-hydroxy-2-methyl-propylthio)-7-hydroxy-1,5-bicyclo-[3.3.0]octane, |
| 95 | 2-Oxa-3-hydroxy-6β-(3-(4-hydroxyphenoxy)-2-hydroxy-2-methyl-propylthio)-7-hydroxy-1,5-bicyclo-[3.3.0]octane, |
| 96 | 2-Oxa-3-hydroxy-6β-(3-(4-methoxyphenoxy)-2-hydroxy-2-methyl-propylthio)-7-hydroxy-1,5-bicyclo[3.3.0]octane, |
| 97 | 2-Oxa-3-hydroxy-6β-(3-(4-tolyloxy)-2-hydroxy-2-methyl-propylthio)-7-hydroxy-1,5-bicyclo[3.3.0]-octane, |
| 98 | 2-Oxa-3-hydroxy-6β-(3-(4-trifluoromethylphenoxy)-2-hydroxy-2-methyl-propylthio)-7-hydroxy-1,5-bicyclo[3.3.0]octane, |
| 99 | 2-Oxa-3-hydroxy-6β-(3-(3-chlorophenoxy-2-hydroxy-2-methyl-propylthio)-7-hydroxy-1,5-bicyclo-[3.3.0]octane, |
| 100 | 2-Oxa-3-hydroxy-6β-(3-(3-methoxyphenoxy)-2-hydroxy-2-methyl-propylthio)-7-hydroxy-1,5-bicyclo[3.3.0]octane, |
| 101 | 2-Oxa-3-hydroxy-6β-(3-(3-trifluoromethylphenoxy)-2-hydroxy-2-methyl-propylthio)-7-hydroxy-1,5-bicyclo[3.3.0]octane, |
| 102 | 2-Oxa-3-hydroxy-6β-(3-(2,4-dichlorophenoxy)-2-hydroxy-2-methyl-propylthio)-7-hydroxy-1,5-bicyclo[3.3.0]octane, |
| 103 | 2-Oxa-3-hydroxy-6β-(3-(2,4-dimethoxyphenoxy)-2-hydroxy-2-methyl-propylthio)-7-hydroxy-1,5-bicyclo[3.3.0]octane, |
| 104 | 2-Oxa-3-hydroxy-6β-(2-(2,4,6-trimethylphenoxy)-2-hydroxy-2-methyl-propylthio)-7-hydroxy-1,5-bicyclo[3.3.0]octane, |
| 105 | 2-Oxa-3-hydroxy-6β-(3-(3,4,5-trimethoxyphenoxy)-2-hydroxy-2-methyl-propylthio)-7-hydroxy-1,5-bicyclo[3.3.0]octane, |
| 106 | 2-Oxa-3-hydroxy-6β-(2-hydroxy-2-methyl-heptylthio)-7-hydroxy-1,5-bicyclo[3.3.0]octane, |
| 107 | 2-Oxa-3-hydroxy-6β-(2-hydroxy-heptylthio)-7-hydroxy-1,5-bicyclo[3.3.0]octane, |
| 108 | 2-Oxa-3-hydroxy-6β-(2-hydroxy-3-methyl-heptylthio)-7-hydroxy-1,5-bicyclo[3.3.0]octane, |
| 109 | 2-Oxa-3-hydroxy-6β-(2-hydroxy-2,3-dimethyl-heptylthio)-7-hydroxy-1,5-bicyclo[3.3.0]octane, |
| 110 | 2-Oxa-3-hydroxy-6β-(2-hydroxy-3,3-dimethyl-heptylthio)-7-hydroxy-1,5-bicyclo[3.3.0]octane, |
| 111 | 2-Oxa-3-hydroxy-6β-(2-hydroxy-3-ethyl-heptylthio)-7-hydroxy-1,5-bicyclo[3.3.0]octane, |
| 112 | 2-Oxa-3-hydroxy-6β-(2-hydroxy-2-methyl-3-ethyl-heptylthio)-7-hydroxy-1,5-bicyclo[3.3.0]octane, |
| 113 | 2-Oxa-3-hydroxy-6β-(2-hydroxy-4-ethyl-heptylthio)-7-hydroxy-1,5-bicyclo[3.3.0]octane, |
| 114 | 2-Oxa-3-hydroxy-6β-(2-hydroxy-2-methyl-4-ethyl-heptylthio)-7-hydroxy-1,5-bicyclo[3.3.0]octane, |
| 115 | 2-Oxa-3-hydroxy-6β-(2-hydroxy-2-methyl-5-methoxy pentylthio)-7-hydroxy-1,5-bicyclo[3.3.0]octane, |
| 116 | 2-Oxa-3-hydroxy-6β-(2-hydroxy-2-methyl-4-ethoxy-butylthio)-7-hydroxy-1,5-bicyclo[3.3.0]octane, |
| 117 | 2-Oxa-3-hydroxy-6β-(2-hydroxy-2-methyl-3-propyloxy-propylthio)-7-hydroxy-1,5-bicyclo-[3.3.0]octane, |
| 118 | 2-Oxa-3-hydroxy-6β-(2-hydroxy-2-methyl-3-butyloxy-propylthio)-7-hydroxy-1,5-bicyclo[3.3.0]octane, |
| 119 | 2-Oxa-3-hydroxy-6β-(2-phenyl-2-hydroxy-propylthio)-7-hydroxy-1,5-bicyclo[3.3.0]octane, |
| 120 | 2-Oxa-3-hydroxy-6β-(2-(4-fluorophenyl)-2-hydroxy-propylthio)-7-hydroxy-1,5-bicyclo[3.3.0]octane, |
| 121 | 2-Oxa-3-hydroxy-6β-(2-(4-chlorophenyl)-2-hydroxy-propylthio)-7-hydroxy-1,5-bicyclo[3.3.0]octane, |
| 122 | 2-Oxa-3-hydroxy-6β-(2-(4-bromophenyl)-2-hydroxy-propylthio)-7-hydroxy-1,5-bicyclo[3.3.0]octane, |
| 123 | 2-Oxa-3-hydroxy-6β-(2-(4-hydroxyphenyl)-2-hydroxy-propylthio)-7-hydroxy-1,5-bicyclo[3.3.0]octane, |
| 124 | 2-Oxa-3-hydroxy-6β-(2-(4-methoxyphenyl)-2-hydroxy-propylthio)-7-hydroxy-1,5-bicyclo[3.3.0]-octane, |
| 125 | 2-Oxa-3-hydroxy-6β-(2-(4-tolyl)-2-hydroxy-propyl- |

| Example | Compound of the formula IV |
|---|---|
| | thio)-7-hydroxy-1,5-bicyclo[3.3.0]octane, |
| 126 | 2-Oxa-3-hydroxy-6β-(2-(4-triflurormethylphenyl)-2-hydroxy-propylthio)-7-hydroxy-1,5-bicyclo-[3.3.0]octane, |
| 127 | 2-Oxa-3-hydroxy-6β-(2-(3-methoxyphenyl)-2-hydroxy-propylthio)-7-hydroxy-1,5-bicyclo[3.3.0]-octane, |
| 128 | 2-Oxa-3-hydroxy-6β-(2-(3-chlorophenyl)-2-hydroxy-propylthio)-7-hydroxy-1,5-bicyclo[3.3.0]octane, |
| 129 | 2-Oxa-3-hydroxy-6β-(2-(3-trifluromethylphenyl)-2-hydroxy-propylthio)-7-hydroxy-1,5-bicyclo-[3.3.0]octane, |
| 130 | 2-Oxa-3-hydroxy-6β-(2-(3,4,5-trimethoxyphenyl)-2-hydroxy-propylthio)-7-hydroxy-1,5-bicyclo-[3.3.0]octane, |
| 131 | 2-Oxa-3-hydroxy-6β-(3-phenyl-2-methyl-2-hydroxy-propylthio)-7-hydroxy-1,5-bicyclo[3.3.0]octane, |
| 132 | 2-Oxa-3-hydroxy-6β-(3-(4-fluorophenyl)-2-methyl-2-hydroxy-propylthio)-7-hydroxy-1,5-bicyclo-[3.3.0]octane, |
| 133 | 2-Oxa-3-hydroxy-6β-(3-(4-chlorophenyl)-2-methyl-2-hydroxy-propylthio)-7-hydroxy-1,5-bicyclo-[3.3.0]octane, |
| 134 | 2-Oxa-3-hydroxy-6β-(3-(4-bromophenyl)-2-methyl-2-hydroxy-propylthio)-7-hydroxy-1,5-bicyclo-[3.3.0]octane, |
| 135 | 2-Oxa-3-hydroxy-6β-(3-(4-methoxyphenyl)-2-methyl-2-hydroxy-propylthio)-7-hydroxy-1,5-bicyclo-[3.3.0]octane, |
| 136 | 2-Oxa-3-hydroxy-6β-(3-(4-tolyl)-2-methyl-2-hydroxy-propylthio)-7-hydroxy-1,5-bicyclo-[3.3.0]octane, |
| 137 | 2-Oxa-3-hydroxy-6β-(3-(4-trifluoromethylphenyl)-2-methyl-2-hydroxy-propylthio)-7-hydroxy-1,5-bicyclo[3.3.0]octane, |
| 138 | 2-Oxa-3-hydroxy-6β-(3-(3-chlorophenyl)-2-methyl-2-hydroxy-propylthio)-7-hydroxy-1,5-bicyclo-[3.3.0]octane, |
| 139 | 2-Oxa-3-hydroxy-6β-(3-(3-trifluoromethylphenyl)-2-methyl-2-hydroxy-propylthio)-7-hydroxy-1,5-bicyclo[3.3.0]octane, |
| 140 | 2-Oxa-3-hydroxy-6β-(4-phenyl-2-hydroxy-butyl-thio)-7-hydroxy-1,5-bicyclo[3.3.0]octane, |
| 141 | 2-Oxa-3-hydroxy-β-(4-(3-chlorophenyl)-2-hydroxy-butylthio)-7-hydroxy-1,5-bicyclo[3.3.0]octane, |
| 142 | 2-Oxa-3-hydroxy-6β-(4-(3-trilfuoromethylphenyl)-2-hydroxy-butylthio)-7-hydroxy-1,5-bicyclo-[3.3.0]octane, |
| 143 | 2-Oxa-3-hydroxy-6β-(4-phenyl-2-methyl-2-hydroxy-butylthio)-7-hydroxy-1,5-bicyclo[3.3.0]octane, |
| 144 | 2-Oxa-3-hydroxy-6β-(4-(3-chlorophenyl)-2-methyl-2-hydroxy-butylthio)-7-hydroxy-1,5-bicyclo-[3.3.0]octane, |
| 145 | 2-Oxa-3-hydroxy-6β-(4-(3-trifluoromethylphenyl)-2-methyl-2-hydroxy-butylthio)-7-hydroxy-1,5-bicyclo[3.3.0]octane, |
| 146 | 2-Oxa-3-hydroxy-6β-(2-(2-naphthyl)-2-hydroxy-propylthio)-7-hydroxy-1,5-bicyclo[3.3.0]-octane, |
| 147 | 2-Oxa-3-hydroxy-6β-(2-(4-pyridyl)-2-hydroxy-propylthio)-7-hydroxy-1,5-bicyclo[3.3.0]octane, |
| 148 | 2-Oxa-3-hydroxy-6β-(2-(2-thienyl)-2-hydroxy-propylthio)-7-hydroxy-1,5-bicyclo[3.3.0]octane, |
| 149 | 2-Oxa-3-hydroxy-6β-(3-(3-chlorophenoxy)-2-tetrahydropyran-2-yl-oxy-propylthio)-7α-tetrahydropyran-2-yl-oxy-1βH,5βH—bicyclo[3.3.0]octane, |
| 150 | 2-Oxa-3-hydroxy-6β-(3-(3-chlorophenoxy)-2-trimethyl-silyloxy-propylthio)-7α-trimethylsilyl-oxy-1βH,5βH—bicyclo[3.3.0]octane. |

EXAMPLE 151

8 g of 2-oxa-3-hydroxy-6β-(3-(3-chlorophenoxy)-2-hydroxy-propylthio)-7α-hydroxy-1βH,5βH-bicyclo[3.3.0]octane is dissolved in 50 ml of tetrahydrofuran (THF) and this solution is added dropwise, while cooling, to a solution of 12.6 g of potassium tert-butylate and 14.8 g of carboxybutyltriphenylphosphonium bromide in 50 ml of THF. The mixture is stirred for a further 1 hour, 50 ml of water is then added dropwise and the THF is distilled off on a rotary evaporator. The resulting aqueous solution is washed three times with ethyl acetate and acidified to pH 3 with citric acid. It is extracted three times with ethyl acetate, the solution is dried over sodium sulfate and the solvent is distilled off on a rotary evaporator. The residue is taken up in 200 ml of diethyl ether and the solution is stored overnight at 0° C. The mixture is filtered, the solvent is distilled off and, after purification by chromatography on 50 g of silica gel, this gives 7.0 g of 9α,11α15-trihydroxy-16-(3-chlorophenoxy)-13-thia-17,18,19,20-tetranor-(Z)-5-prostenoic acid.

IR: 1,710, 2,400, 3,650 cm$^{-1}$.

NMR: 1.1–2.6; 2.6–3.1; 4.05; 4.2; 5.3; 5.4; 6.6–7.4.

Analogously to Example 51, the compounds of formula III mentioned in the following Examples 152 to 223 are obtainable from the compounds of formula IV mentioned in Examples 77 to 148, by reaction with carboxybutyltriphenylphosphonium bromide in the presence of potassium tert-butylate:

| Example | Compound of the formula III in which D = —CHOH— and E = —CH=CH— |
|---|---|
| 152 | 9,11,15-Trihydroxy-16-phenoxy-13-thia-17,18,19,20-tetranor-5-prostenoic acid, |
| 153 | 9,11,15-Trihydroxy-16-(4-fluorophenoxy)-13-thia-17,18,19,20-tetranor-5-prostenoic acid, IR: 1,710, 2,700, 2,940, 3,700 cm$^{-1}$ NMR: 1.1–2.6; 2.7–3.1; 4.05; 4.2; 5.3; 5.45; 6.85; 6.95; |
| 154 | 9,11,15-Trihydroxy-16-(4-chlorophenoxy)-13-thia-17,18,19,20-tetranor-5-prostenoic acid, |
| 155 | 9,11,15-Trihydroxy-16-(4-bromophenoxy)-13-thia-17,18,19,20-tetranor-5-prostenoic acid, |
| 156 | 9,11,15-Trihydroxy-16-(4-hydroxyphenoxy)-13-thia-17,18,19,20-tetranor-5-prostenoic acid, |
| 157 | 9,11,15-Trihydroxy-16-(4-methoxyphenoxy)-13-thia-17,18,19,20-tetranor-5-prostenoic acid, |
| 158 | 9,11,15-Trihydroxy-16-(4-tolyloxy,)-13-thia-17,18,19,20-tetranor-5-prostenoic acid, |
| 159 | 9,11,15-Trihydroxy-16-(4-trifluoromethylphenoxy)-13-thia-17,18,19,20-tetranor-5-prostenoic acid, |
| 160 | 9,11,15-Trihydroxy-16-(3-methoxyphenoxy)-13-thia-17,18,19,20-tetranor-5-prostenoic acid, |
| 161 | 9,11,15-Trihydroxy-16-(3-trifluoromethylphenoxy)-13-thia-17,18,19,20-tetranor-5-prostenoic acid, |
| 162 | 9,11,15-Trihydroxy-16-(2,4-dichlorophenoxy)-13-thia-17,18,19,20-tetranor-5-prostenoic acid, |
| 163 | 9,11,15-Trihydroxy-16-(2,4-dimethoxyphenoxy)-13-thia-17,18,19,20-tetranor-5-prostenoic acid, |
| 164 | 9,11,15-Trihydroxy-16-(2,4,6-trimethylphenoxy)-13-thia-17,18,19,20-tetranor-5-prostenoic acid, |
| 165 | 9,11,15-Trihydroxy-16-(3,4,5-trimethoxyphenoxy)-13-thia-17,18,19,20-tetranor-5-prostenoic acid, |
| 166 | 9,11,15-Trihydroxy-15-methyl-16-phenoxy-13-thia-17,18,19,20-tetranor-5-prostenoic acid, |
| 167 | 9,11,15-Trihydroxy-15-methyl-16-(4-fluorophenoxy)-13-thia-17,18,19,20-tetranor-5-prostenoic acid, |
| 168 | 9,11,15-Trihydroxy-15-methyl-16-(4-chlorophenoxy)-13-thia-17,18,19,20-tetranor-5-prostenoic acid, |
| 169 | 9,11,15-Trihydroxy-15-methyl-16-(4-bromophenoxy)-13-thia-17,18,19,20-tetranor-5-prostenoic acid, |
| 170 | 9,11,15-Trihydroxy-15-methyl-16-(4-hydroxyphenoxy)-13-thia-17,18,19,20-tetranor-5-prostenoic acid, |
| 171 | 9,11,15-Trihydroxy-15-methyl-16-(4-methoxyphenoxy)-13-thia-17,18,19,20-tetranor-5-prostenoic acid, |
| 172 | 9,11,15-Trihydroxy-15-methyl-16-(4-tolyloxy)-13-thia-17,18,19,20-tetranor-5-prostenoic acid, |
| 173 | 9,11,15-Trihydroxy-15-methyl-16-(4-trifluoromethylphenoxy)-13-thia-17,18,19,20-tetranor-5-prostenoic acid, |
| 174 | 9,11,15-Trihydroxy-15-methyl-16-(3-chlorophenoxy)-13-thia-17,18,19,20-tetranor-5-prostenoic acid, IR: 1,600, 1,710, 2,900, 3,400 cm$^{-1}$ NMR: 1.4; 4.20; 4.95; 5.45; 6.7–7.3; |

| Example | Compound of the formula III in which D = —CHOH— and E = —CH=CH— |
|---|---|
| 175 | 9,11,15-Trihydroxy-15-methyl-16-(3-methoxyphenoxy)-13-thia-17,18,19,20-tetranor-5-prostenoic acid, |
| 176 | 9,11,15-Trihydroxy-15-methyl-16-(3-trifluoromethylphenoxy)-13-thia-17,18,19,20-tetranor-5-prostenoic acid, |
| 177 | 9,11,15-Trihydroxy-15-methyl-16-(2,4-dichlorophenoxy)-13-thia-17,18,19,20-tetranor-5-prostenoic acid, |
| 178 | 9,11,15-Trihydroxy-15-methyl-16-(2,4-dimethoxyphenoxy)-13-thia-17,18,19,20-tetranor-5-prostenoic acid, |
| 179 | 9,11,15-Trihydroxy-15-methyl-16-(2,4,6-trimethylphenoxy)-13-thia-17,18,19,20-tetranor-5-prostenoic acid, |
| 180 | 9,11,15-Trihydroxy-15-methyl-16-(3,4,5-trimethoxy-phenoxy)-13-thia-17,18,19,20-tetranor-5-prostenoic acid, |
| 181 | 9,11,15-Trihydroxy-15-methyl-13-thia-5-prostenoic acid IR: 1,710, 2,200, 3,700 cm$^{-1}$, NMR: 0.85; 1.2; 1.0–2.6; 2.6–3.05; 4.15; 5.1–5.4; |
| 182 | 9,11,15-Trihydroxy-13-thia-5-prostenoic acid, |
| 183 | 9,11,15-Trihydroxy-16-methyl-13-thia-5-prostenoic acid, |
| 184 | 9,11,15-Trihydroxy-15,16-dimethyl-13-thia-5-prostenoic acid, |
| 185 | 9,11,15-Trihydroxy-16,16-dimethyl-13-thia-5-prostenoic acid, |
| 186 | 9,11,15-Trihydroxy-16-ethyl-13-thia-5-prostenoic acid, |
| 187 | 9,11,15-Trihydroxy-15-methyl-16-ethyl-13-thia-5-prostenoic acid, |
| 188 | 9,11,15-Trihydroxy-17-ethyl-13-thia-5-prostenoic acid, |
| 189 | 9,11,15-Trihydroxy-15-methyl-17-ethyl-13-thia-5-prostenoic acid, |
| 190 | 9,11,15-Trihydroxy-15-methyl-13-thia-19-oxa-5-prostenoic acid, |
| 191 | 9,11,15-Trihydroxy-15-methyl-13-thia-18-oxa-5-prostenoic acid, |
| 192 | 9,11,15-Trihydroxy-15-methyl-13-thia-17-oxa-5-prostenoic acid, |
| 193 | 9,11,15-Trihydroxy-15-methyl-13-thia-17-oxa-20-homo-5-prostenoic acid, |
| 194 | 9,11,15-Trihydroxy-15-phenyl-13-thia-17,18,19,20-tetranor-5-prostenoic acid, |
| 195 | 9,11,15-Trihydroxy-15-(4-fluorophenyl)-13-thia-17,18,19,20-tetranor-5-prostenoic acid, |
| 196 | 9,11,15-Trihydroxy-15-(4-chlorophenyl)-13-thia-17,18,19,20-tetranor-5-prostenoic acid, |
| 197 | 9,11,15-Trihydroxy-15-(4-bromophenyl)-13-thia-17,18,19,20-tetranor-5-prostenoic acid, |
| 198 | 9,11,15-Trihydroxy-15-(4-hydroxyphenyl)-13-thia-17,18,19,20-tetranor-5-prostenoic acid, |
| 199 | 9,11,15-Trihydroxy-15-(4-methoxyphenyl)-13-thia-17,18,19,20-tetranor-5-prostenoic acid, |
| 200 | 9,11,15-Trihydroxy-15-(4-tolyl)-13-thia-17,18,19,20-tetranor-5-prostenoic acid, |
| 201 | 9,11,15-Trihydroxy-15-(4-trifluoromethylphenyl)-13-thia-17,18,19,20-tetranor-5-prostenoic acid, |
| 202 | 9,11,15-Trihydroxy-15-(3-methoxyphenyl)-13-thia-17,18,19,20-tetranor-5-prostenoic acid, |
| 203 | 9,11,15-Trihydroxy-15-(3-chlorophenyl)-13-thia-17,18,19,20-tetranor-5-prostenoic acid, |
| 204 | 9,11,15-Trihydroxy-15-(3-trifluoromethylphenyl)-13-thia-17,18,19,20-tetranor-5-prostenoic acid, |
| 205 | 9,11,15-Trihydroxy-15-(3,4,5-trimethoxyphenyl)-13-thia-17,18,19,20-tetranor-5-prostenoic acid, |
| 206 | 9,11,15-Trihydroxy-15-methyl-16-phenyl-13-thia-17,18,19,20-tetranor-5-prostenoic acid, |
| 207 | 9,11,15-Trihydroxy-15-methyl-16-(4-fluorophenyl)-13-thia-17,18,19,20-tetranor-5-prostenoic acid, |
| 208 | 9,11,15-Trihydroxy-15-methyl-16-(4-chlorophenyl)-13-thia-17,18,19,20-tetranor-5-prostenoic acid, |
| 209 | 9,11,15-Trihydroxy-15-methyl-16-(4-bromophenyl)-13-thia-17,18,19,20-tetranor-5-prostenoic acid, |
| 210 | 9,11,15-Trihydroxy-15-methyl-16-(4-methoxyphenyl)-13-thia-17,18,19,20-tetranor-5-prostenoic acid, |
| 211 | 9,11,15-Trihydroxy-15-methyl-16-(4-tolyl)-13-thia-17,18,19,20-tetranor-5-prostenoic acid, |
| 212 | 9,11,15-Trihydroxy-15-methyl-16-(4-trifluoromethyl-phenyl)-13-thia-17,18,19,20-tetranor-5-prostenoic acid, |
| 213 | 9,11,15-Trihydroxy-15-methyl-16-(3-chlorophenyl)-13-thia-17,18,19,20-tetranor-5-prostenoic acid, |
| 214 | 9,11,15-Trihydroxy-15-methyl-16-(3-trifluoromethyl-phenyl)-13-thia-17,18,19,20-tetranor-5-prostenoic acid, |
| 215 | 9,11,15-Trihydroxy-17-phenyl-13-thia-18,19,20-trinor-5-prostenoic acid, |
| 216 | 9,11,15-Trihydroxy-17-(3-chlorophenyl)-13-thia-18,19,20-trinor-5-prostenoic acid, |
| 217 | 9,11,15-Trihydroxy-17-(3-trifluoromethylphenyl)-13-thia-18,19,20-trinor-5-prostenoic acid, |
| 218 | 9,11,15-Trihydroxy-15-methyl-17-phenyl-13-thia-18,19,20-trinor-5-prostenoic acid, IR: 1,600, 1,700, 2,950, 3,400 cm$^{-1}$; NMR: 1.35; 4.18; 5.42; 7.22; |
| 219 | 9,11,15-Trihydroxy-15-methyl-17-(3-chlorophenyl)-13-thia-18,19,20-trinor-5-prostenoic acid, IR: 1,050, 1,240, 1,600, 1,710, 2,900, 3,400 cm$^{-1}$ NMR: 1.32; 4.0–4.3; 5.35; 7.0–7.2; |
| 220 | 9,11,15-Trihydroxy-15-methyl-17-(3-trifluoromethylphenyl)-23-thia-18,19,20-trinor-5-prostenoic acid, IR: 1,720, 3,450 cm$^{-1}$ NMR: 1.35; 5.25; 5.48; 7.45; |
| 221 | 9,11,15-Trihydroxy-15-(2-naphthyl)-13-thia-17,18,19,20-tetranor-5-prostenoic acid, |
| 222 | 9,11,15-Trihydroxy-15-(4-pyridyl)-13-thia-17,18,19,20-tetranor-5-prostenoic acid, |
| 223 | 9,11,15-Trihydroxy-15-(2-thienyl)-13-thia-17,18,19,20-tetranor-5-prostenoic acid. |

EXAMPLE 224

A solution of 5.6 g of 4-(4-benzamido)-phenoxycarbonylbutyltriphenylphosphonium bromide dissolved in 15 ml of dry THF is added dropwise, under nitrogen, to a stirred solution which has been obtained by adding 2 g of potassium tert-butylate to 10 ml of dry THF. 3 g of 2-oxa-3,7-dihydroxy-6β-(2-hydroxy-2-methylheptylthio)-1,5-bicyclo[3.3.0]octane, dissolved in 5 ml of dry THF, is then added dropwise, under nitrogen and while stirring, to the solution of the phosphorylide and the reaction mixture is stirred for 1 hour at room temperature. It is then poured into a mixture consisting of 10 ml of ethyl acetate, 40 g of solid carbon dioxide and 50 ml of water, the organic phase is separated off, the aqueous phase is washed with three times 50 ml of ethyl acetate containing 20 g of solid carbon dioxide, the combined organic phases are washed with water and dried over MgSO$_4$, the solvent is distilled off and, after purification of the residue by chromatography (silica gel/chloroform), this gives p-benzoylaminophenyl 9,11,15-trihydroxy-15-methyl-13-thia-5-prostenoate.

EXAMPLE 225

1 g of 9α,11α,15-trihydroxy-16-(3-chlorophenoxy)-13-thia-17,18,19,20-tetranor-(Z)-5-prostenoic acid is dissolved in 10 ml of ethyl acetate, hydrogen is passed through the solution for 10 minutes, 0.1 g of palladium-on-charcoal is then added and hydrogenation is carried out with 1 atmosphere of hydrogen until the calculated amount of hydrogen has been taken up. After the reaction has ended, the catalyst is filtered off and the solvent is distilled off. This gives a yellow oil, which is taken up in ether. On cooling, 0.8 g of 9α,11α,15-trihydroxy-16-

(3-chlorophenoxy)-13-thia-17,18,19,20-tetranor-prostanoic acid crystallizes.

IR: 1,600, 1,710, 2,950, 3,400 cm$^{-1}$.

NMR: 1.1–2.6; 2.7–3.1; 4.1; 4.2; 6.7–7.3.

Analogously to example 225, catalytic hydrogenation of the compounds of formula III mentioned in Examples 152 to 223 affords the corresponding 9,11,15-trihydroxy-13-thiaprostanoic acid derivatives, especially the compounds mentioned in the following Examples 226 to 255:

| Example | Compound of the formula III in which D = —CHOH— and E = —CH$_2$—CH$_2$— |
|---|---|
| 226 | 9,11,15-Trihydroxy-16-phenoxy-13-thia-17,18,19,20-tetranor-prostanoic acid, |
| 227 | 9,11,15-Trihydroxy-16-(4-fluorophenoxy)-13-thia-17,18,19,20-tetranor-prostanoic acid, |
| 228 | 9,11,15-Trihydroxy-16-(4-chlorophenoxy)-13-thia-17,18,19,20-tetranor-prostanoic acid, |
| 229 | 9,11,15-Trihydroxy-16-(4-trifluoromethylphenoxy)-13-thia-17,18,19,20-tetranor-prostanoic acid, |
| 230 | 9,11,15-Trihydroxy-16-(3-trifluoromethylphenoxy)-13-thia-17,18,19,20-tetranor-prostanoic acid, IR: 1,590, 1,700, 2,900, 3,400 cm$^{-1}$ NMR: 1.1–2.5; 4.0; 4.2–4.4; 6.9–7.4; |
| 231 | 9,11,15-Trihydroxy-15-methyl-16-(4-fluorophenoxy)-13-thia-17,18,19,20-tetranor-prostanoic acid, IR: 1,220, 1,710, 3,400 cm$^{-1}$ NMR: 1.37; 2.3; 3.85; 4.14; 6.7–7.0; |
| 232 | 9,11,15-Trihydroxy-15-methyl-16-(4-chlorophenoxy)-13-thia-17,18,19,20-tetranor prostanoic acid, |
| 233 | 9,11,15-Trihydroxy-15-methyl-16-(4-trifluoromethylphenoxy)-13-thia-17,18,19,20-tetranor-prostanoic acid, |
| 234 | 9,11,15-Trihydroxy-15-methyl-16-chlorophenoxy)-13-thia-17,18,19,20-tetranor-prostanoic acid, |
| 235 | 9,11,15-Trihydroxy-15-methyl-16-(3-trifluoromethylphenoxy)-13-thia-17,18,19,20-tetranor-prostanoic acid, |
| 236 | 9,11,15-Trihydroxy-15-methyl-13-thia-prostanoic acid IR: 1,705, 2,680 and 3,340 cm$^{-1}$ NMR: 0.89; 1.22; 2.3; 4.18; 5.03; |
| 237 | 9,11,15-Trihydroxy-13-thia-prostanoic acid, |
| 238 | 9,11,15-Trihydroxy-16-methyl-13-thia-prostanoic acid, |
| 239 | 9,11,15-Trihydroxy-15,16-dimethyl-13-thia-prostanoic acid, |
| 240 | 9,11,15-Trihydroxy-16,16-dimethyl-13-thia-prostanoic acid, |
| 241 | 9,11,15-Trihydroxy-15-phenyl-13-thia-17,18,19,20-tetranor-prostanoic acid, |
| 242 | 9,11,15-Trihydroxy-15-(4-fluorophenyl)-13-thia-17,18,19,20-tetranor-prostanoic acid, |
| 243 | 9,11,15-Trihydroxy-15-(4-chlorophenyl)-13-thia-17,18,19,20-tetranor-prostanoic acid, |
| 244 | 9,11,15-Trihydroxy-15-(4-tolyl)-13-thia-17,18,19,20-tetranor-prostanoic acid, IR: 1,505, 1,705, 3,350 cm$^{-1}$ NMR: 1.2; 2.3; 4.2; 4.6; 7.0–7.3; |
| 245 | 9,11,15-Trihydroxy-15-(3-chlorophenyl)-13-thia-17,18,19,20-tetranor-prostanoic acid, |
| 246 | 9,11,15-Trihydroxy-15-(3-trifluoromethylphenyl)-13-thia-17,18,19,20-tetranor-prostanoic acid, |
| 247 | 9,11,15-Trihydroxy-15-methyl-16-phenyl-13-thia-17,18,19,20-tetranor-prostanoic acid, |
| 248 | 9,11,15-Trihydroxy-15-methyl-16-(4-fluorophenyl)-13-thia-17,18,19,20-tetranor-prostanoic acid, |
| 249 | 9,11,15-Trihydroxy-15-methyl-16-(4-tolyl)-13-thia-17,18,19,20-tetranor-prostanoic acid, |
| 250 | 9,11,15-Trihydroxy-17-phenyl-13-thia-18,19,20-trinor-prostanoic acid, |
| 251 | 9,11,15-Trihydroxy-17-(3-chlorophenyl)-13-thia-18,19,20-trinor-prostanoic acid, |
| 252 | 9,11,15-Trihydroxy-17-(3-trifluoromethylphenyl)-13-thia-18,19,20-trinor-prostanoic acid, |
| 253 | 9,11,15-Trihydroxy-15-methyl-17-phenyl-13-thia-18,19,20-trinor prostanoic acid, IR: 1,700, 3,400 cm$^{-1}$ NMR: 1.33; 4.4; 7.25; |
| 254 | 9,11,15-Trihydroxy-15-methyl-17-(3-chlorophenyl)-13-thia-18,19,20-trinor prostanoic acid, |
| 255 | 9,11,15-Trihydroxy-15-methyl-17-(3-trifluoromethylphenyl)-13-thia-18,19,20-trinor-prostanoic acid. |

EXAMPLE 256

0.44 g of 9α,11α,15-trihydroxy-16-(3-chlorophenoxy)-13-thia-17,18,19,20-tetranor-prostanoic acid, 0.22 g of triethylamine, 0.037 g of dimethylamino-pyridine and 0.33 g of tert-butyldimethylsilyl chloride are dissolved in 10 ml of methylene chloride, at 0° C., under a nitrogen atmosphere. The solution is left to warm up to room temperature and stirred overnight. The precipitate is then filtered off with suction, the filtrate is washed twice with saturated ammonium chloride solution and dried over MgSO$_4$ and the solvent is stripped off on a rotary evaporator.

The residue is dissolved in acetone, an ice-cold solution of 0.15 ml of 8 N Jones reagent (chromic anhydride in dilute sulfuric acid) in 5 ml of acetone is added dropwise at −20° C., the mixture is stirred for one hour and excess chromic acid is then destroyed with 1 ml of isopropanol. The mixture is then left to warm up to room temperature, 10 ml of 10% sulfuric acid is added and the mixture is stirred for a further hour at room temperature. The acetone is stripped off on a rotary evaporator and the aqueous phase is extracted three times with methylene chloride. The combined organic phases are dried over MgSO$_4$ and concentrated to a residue. The residue is chromatographed with ether on 50 g of silica gel. This gives 255 mg of crystalline 11α,15-dihydroxy-9-oxo-16-(3-chlorophenoxy)-13-thia-17,18,19, 20,-tetranor-prostanoic acid.

Analogously to Example 256, oxidation of compounds of formula III in which D=—CHOH—and E=—CH$_2$—CH$_2$— affords the corresponding compounds in which D=—CO—, especially the compounds mentioned in the following examples 257–293:

| Example | Compound of the formula III in which D = —CO— and E = —CH$_2$—CH$_2$— |
|---|---|
| 257 | 11,15-Dihydroxy-9-oxo-16-phenoxy-13-thia-17,18,19,20-tetranor-prostanoic acid, |
| 258 | 11,15-Dihydroxy-9-oxo-16-(4-fluorophenoxy)-13-thia-17,18,19,20-tetranor-prostanoic acid, |
| 259 | 11,15-Dihydroxy-9-oxo-16-(4-methoxyphenoxy)-13-thia-17,18,19,20-tetranor-prostanoic acid, |
| 260 | 11,15-Dihydroxy-9-oxo-16-(3-trifluoromethylphenoxy)-13-thia-17,18,19,20-tetranor-prostanoic acid, IR: 1,230, 1,490, 1,590, 1,700, 1,730, 2,950 3,410 cm$^{-1}$ NMR: 2.3; 4.1; 4.2–4.5; 7.0–7.5; |
| 261 | 11,15-Dihydroxy-9-oxo-15-methyl-16-phenoxy-13-thia-17,18,19,20-tetranor-prostanoic acid, |
| 262 | 11,15-Dihydroxy-9-oxo-15-methyl-16-(4-fluorophenoxy)-13-thia-17,18,19,20-tetranor-prostanoic acid, IR: 1,215, 1,500, 1,710, 1,740, 3,350 cm$^{-1}$ NMR: 1.4; 2.3; 3.9; 4.3; 6.8–7.1; |
| 263 | 11,15-Dihydroxy-9-oxo-15-methyl-16-(4-chlorophenoxy)-13-thia-17,18,19,20-tetranor-prostanoic acid, |
| 264 | 11,15-Dihydroxy-9-oxo-15-methyl-16-(4-methoxyphenoxy)-13-thia-17,18,19,20-tetranor- |

| Example | Compound of the formula III in which D = —CO— and E = —CH$_2$—CH$_2$— |
|---|---|
| | prostanoic acid, |
| 265 | 11,15-Dihydroxy-9-oxo-15-methyl-16-(3-trifluoromethylphenoxy)-13-thia-17,18,19,20-tetranor-prostanoic acid,<br>IR: 1,230, 1,480, 1,590, 1,710, 1,740, 2,900, 3,400 cm$^{-1}$<br>NMR: 1.35; 2.25; 3.9; 4.3; 6.9–7.4; |
| 266 | 11,15-Dihydroxy-9-oxo-15-methyl-13-thia-prostanoic acid,<br>IR: 1,710, 1,740, 3,450 cm$^{-1}$<br>NMR: 0.85; 1.2; 2.3; 4.2; 5.8; |
| 267 | 11,15-Dihydroxy-9-oxo-13-thia-prostanoic acid, |
| 268 | 11,15-Dihydroxy-9-oxo-16-methyl-13-thia-prostanoic acid,<br>IR: 1,700, 1,720, 3,350 cm$^{-1}$<br>NMR: 0.94; 3.68; 4.27; 5.88; |
| 269 | 11,15-Dihydroxy-9-oxo-15,16-dimethyl-13-thia-prostanoic acid,<br>IR: 1,710, 1,740, 3,400 cm$^{-1}$<br>NMR: 0.88; 0.97; 1.2; 4.3; 6.0; |
| 270 | 11,15-Dihydroxy-9-oxo-16,16-dimethyl-13-thia-prostanoic acid, |
| 271 | 11,15-Dihydroxy-9-oxo-17-ethyl-13-thia-prostanoic acid,<br>IR: 1,720; 1,740, 3,450 cm$^{-1}$;<br>NMR: 3.9; 4.29; 5.86; |
| 272 | 11,15-Dihydroxy-9-oxo-15-methyl-13-thia-19-oxa-prostanoic acid,<br>IR: 1,710, 1,740, 3,400 cm$^{-1}$<br>NMR: 1.27; 2.32; 3.31; 422; |
| 273 | 11,15-Dihydroxy-9-oxo-15-methyl-13-thia-18-oxa-prostanoic acid,<br>IR: 1,715, 1,740, 3,400 cm$^{-1}$<br>NMR: 1.21; 1.32; 2.31; 3.50; 4.28; |
| 274 | 11,15-Dihydroxy-9-oxo-15-phenyl-13-thia-16,17,18,19,20-pentanor-prostanoic acid, |
| 275 | 11,15-Dihydroxy-9-oxo-15-(4-tolyl)-13-thia-16,17,18,19,20-pentanor-prostanoic acid,<br>IR: 1,710, 1,740, 3,400 cm$^{-1}$<br>NMR: 2.3; 4.21; 7.15–7.4; |
| 276 | 11,15-Dihydroxy-9-oxo-15-phenyl-13-thia-17,18,19,20-tetranor-prostanoic acid, |
| 277 | 11,15-Dihydroxy-9-oxo-15-(4-fluorophenyl)-13-thia-17,18,19,20-tetranor-prostanoic acid,<br>IR: 1,220, 1,505, 1,605, 1,708, 1,740, 3,400 cm$^{-1}$<br>NMR: 1.61; 2.3; 4.2; 6.9–7.15; 7.3–7.5; |
| 278 | 11,15-Dihydroxy-9-oxo-15-(4-chlorophenyl)-13-thia-17,18,19,20-tetranor-prostanoic acid,<br>IR: 1,710, 1,740, 3,400 cm$^{-1}$<br>NMR: 1.65; 2.3; 4.25; 7.3; |
| 279 | 11,15-Dihydroxy-9-oxo-15-(4-methoxyphenyl)-13-thia-17,18,19,20-tetranor-prostanoic acid, |
| 280 | 11,15-Dihydroxy-9-oxo-15-(4-tolyl)-13-thia-17,18,19,20-tetranor prostanoic acid,<br>IR: 1,510, 1,707, 1,740, 3,400 cm$^{-1}$<br>NMR: 1.6; 2.3; 4.2; 7.1–7.5; |
| 281 | 11,15-Dihydroxy-9-oxo-15-(3-trifluoromethylphenyl)-13-thia-17,18,19,20-tetranor-prostanoic acid, |
| 282 | 11,15-Dihydroxy-9-oxo-15-(3,4,5-trimethoxyphenyl)-13-thia-17,18,19,20-tetranor-prostanoic acid,<br>IR: 1,130, 1,600, 1,670, 1,710, 1,740, 2,950, 3,450 cm$^{-1}$;<br>NMR: 1.63; 2.3; 3.8; 4.23; 5.4; 6.63; |
| 283 | 11,15-Dihydroxy-9-oxo-15-methyl-16-phenyl-13-thia-17,18,19,20-tetranor-prostanoic acid,<br>IR: 1,500, 1,715, 1,745, 3,450 cm$^{-1}$<br>NMR: 1.2; 2.35; 5.0; 7.3; |
| 284 | 11,15-Dihydroxy-9-oxo-15-methyl-16-(4-fluorophenyl)-13-thia-17,18,19,20-tetranor-prostanoic acid, |
| 285 | 11,15-Dihydroxy-9-oxo-15-methyl-16-(4-chlorophenyl)-13-thia-17,18,19,20-tetranor-prostanoic acid, |
| 286 | 11,15-Dihydroxy-9-oxo-15-methyl-16-(4-tolyl)-13-thia-17,18,19,20-tetranor-prostanoic acid, |
| 287 | 11,15-Dihydroxy-9-oxo-15-methyl-16-(3-chlorophenyl)-13-thia-17,18,19,20-tetranor-prostanoic acid,<br>IR: 1,400, 1,495, 1,705, 1,740, 2,950, 3,450 cm$^{-1}$<br>NMR: 1.25; 2.35; 4.3; 5.6; 7.0–7.4; |
| 288 | 11,15-Dihydroxy-9-oxo-15-methyl-16-(3-trifluoromethyl-phenyl)-13-thia-17,18,19,20-tetranor-prostanoic acid, |
| 289 | 11,15-Dihydroxy-9-oxo-17-phenyl-13-thia-18,19,20-trinor-prostanoic acid, |
| 290 | 11,15-Dihydroxy-9-oxo-15-methyl-17-phenyl-13-thia-18,19,20-trinor-prostanoic acid,<br>IR: 1,710, 1,730, 3,400 cm$^{-1}$<br>NMR: 1.35; 5.3; 7.25; |
| 291 | 11,15-Dihydroxy-9-oxo-15-(2-naphthyl)-13-thia-17,18,19,20-tetranor-prostanoic acid,<br>IR: 1,600, 1,705, 1,740, 2,900, 3,400 cm$^{-1}$<br>NMR: 1.76; 2.28; 4.2; 7.42; 7.8; |
| 292 | 11,15-Dihydroxy-9-oxo-16-(4-pyridyl)-13-thia-17,18,19,20-tetranor-prostanoic acid, |
| 293 | 11,15-Dihydroxy-9-oxo-15-(2-thienyl)-13-thia-17,18,19,20-tetranor-prostanoic acid. |

Analogously to Example 256, oxidation of compounds of formula III in which D=—CHOH—and E=—CH=CH—affords the corresponding compounds in which D=—CO—, especially the compounds mentioned in the following Examples 294 to 306:

| Example | Compound of the formula III in which D = —CO— and E = —CH=CH— |
|---|---|
| 295 | 11,15-Dihydroxy-9-oxo-15-methyl-16-phenoxy-13-thia-17,18,19,20-tetranor-5-prostenoic acid, |
| 296 | 11,15-Dihydroxy-9-oxo-15-methyl-16-(4-fluorophenoxy)-13-thia-17,18,19,20-tetranor-5-prostenoic acid, |
| 297 | 11,15-Dihydroxy-9-oxo-15-methyl-16-(4-tolyloxy)-13-thia-17,18,19,20-tetranor-5-prostenoic acid, |
| 298 | 11,15-Dihydroxy-9-oxo-15-methyl-13-thia-5-prostenoic acid,<br>IR: 1,710, 1,740, 2,900, 3,400 cm$^{-1}$<br>NMR: 1.27; 2.32; 4.22; 5.43; |
| 299 | 11,15-Dihydroxy-9-oxo-15-phenyl-13-thia-17,18,19,20-tetranor-5-prostenoic acid, |
| 300 | 11,15-Dihydroxy-9-oxo-15-(4-fluorophenyl)-13-thia-17,18,19,20-tetranor-5-prostenoic acid, |
| 301 | 11,15-Dihydroxy-9-oxo-15-(4-tolyl)-13-thia-17,18,19,20-tetranor-5-prostenoic acid, |
| 302 | 11,15-Dihydroxy-9-oxo-15-methyl-16-phenyl-13-thia-17,18,19,20-tetranor-5-prostenoic acid, |
| 303 | 11,15-Dihydroxy-9-oxo-15-methyl-16-(4-fluorophenyl)-13-thia-17,18,19,20-tetranor-5-prostenoic acid, |
| 304 | 11,15-Dihydroxy-9-oxo-15-methyl-16-(3-trifluoromethylphenyl)-13-thia-17,18,19,20-tetranor-5-prostenoic acid, |
| 305 | 11,15-Dihydroxy-9-oxo-17-phenyl-13-thia-18,19,20-trinor-5-prostenoic acid, |
| 306 | 11,15-Dihydroxy-9-oxo-15-methyl-17-phenyl-13-thia-18,19,20-trinor-5-prostenoic acid. |

EXAMPLE 307

100 mg of 9,11,15-trihydroxy-16-(3-chlorophenoxy)-13-thia-17,18,19,20-tetranor-5-prostenoic acid, dissolved in 10 ml of diethyl ether, is treated with excess ethereal diazomethane solution until no further evolution of nitrogen can be determined. The solvent is distilled off and, after purification of the residue by chromatography (silica gel/benzene: chloroform =1:1), this gives methyl 9,11,15-trihydroxy-16-(3-chlorophenoxy)-13-thia-17,18,19,20-tetranor-5-prostenoate.

Analogously to Example 307, reaction of the compounds of formula III which can be prepared according to Examples 152 to 306, with diazomethane, affords the corresponding methyl esters, especially the methyl esters mentioned in the following Examples 308 to 346:

| Example | Methyl ester of the formula III |
|---|---|
| 308 | Methyl 9,11,15-trihydroxy-16-(4-fluorophenoxy)-13-thia-17,18,19,20-tetranor-5-prostenoate, |
| 309 | Methyl 9,11,15-trihydroxy-16-(3-trifluoromethylphenoxy)-13-thia-17,18,19,20-tetranor-5-prostenoate, |
| 310 | Methyl 9,11,15-trihydroxy-15-methyl-16-(4-tolyloxy)-13-thia-17,18,19,20-tetranor-5-prostenoate, |
| 311 | Methyl 9,11,15-trihydroxy-15-methyl-16-(3-chlorophenoxy)-13-thia-17,18,19,20-tetranor-5-prostenoate, |
| 312 | Methyl 9,11,15-trihydroxy-15-methyl-13-thia-5-prostenoate, |
| 313 | Methyl 9,11,15-trihydroxy-16-methyl-13-thia-5-prostenoate, |
| 314 | Methyl 9,11,15-trihydroxy-15,16-dimethyl-13-thia-17,18,19,20-tetranor-5-prostenoate, |
| 315 | Methyl 9,11,15-trihydroxy-15-phenyl-13-thia-17,18,19,20-tetranor-5-prostenoate, |
| 316 | Methyl 9,11,15-trihydroxy-15-(4-fluorophenyl)-13-thia-17,18,19,20-tetranor-5-prostenoate, |
| 317 | Methyl 9,11,15-trihydroxy-15-(4-methoxyphenyl)-13-thia-17,18,19,20-tetranor-5-prostenoate, |
| 318 | Methyl 9,11,15-trihydroxy-15-methyl-16-(3-chlorophenyl)-13-thia-17,18,19,20-tetranor-5-prostenoate, |
| 319 | Methyl 9,11,15-trihydroxy-15-methyl-17-phenyl-13-thia-18,19,20-trinor-5-prostenoate, |
| 320 | Methyl 9,11,15-trihydroxy-15-methyl-17-(3-chlorophenyl)-13-thia-18,19,20-trinor-5-prostenoate, |
| 321 | Methyl 9,11,15-trihydroxy-15-methyl-17-(3-trifluoromethylphenyl)-13-thia-18,19,20-trinor-5-prostenoate, |
| 322 | Methyl 9,11,15-trihydroxy-16-phenoxy-13-thia-17,18,19,20-tetranor-prostanoate, |
| 323 | Methyl 9,11,15-trihydroxy-15-methyl-16-(4-fluorophenoxy)-13-thia-17,18,19,20-tetranorprostanoate, |
| 324 | Methyl 9,11,15-trihydroxy-15-methyl-13-thia-prostanoate, IR: 1,740, 3,490 cm$^{-1}$ NMR: 0.90; 1.22; 2.31; 3.61; 4.18; |
| 325 | Methyl 9,11,15-trihydroxy-13-thia-prostanoate, |
| 326 | Methyl 9,11,15-trihydroxy-15-16-dimethyl-13-thia-prostanoate, |
| 327 | Methyl 9,11,15-trihydroxy-15-(4-tolyl)-13-thia-17,18,19,20-tetranor-prostanoate, |
| 328 | Methyl 9,11,15-trihydroxy-15-methyl-16-(4-fluorophenyl)-13-thia-17,18,19,20-tetranor-prostanoate, |
| 329 | Methyl 11,15-dihydroxy-9-oxo-16-(3-trifluoromethylphenoxy)-13-thia-17,18,19,20-tetranor-prostanoate, |
| 330 | Methyl 11,15-dihydroxy-9-oxo-15-methyl-16-(4-fluorophenoxy)-13-thia-17,18,19,20-tetranor-prostanoate, |
| 331 | Methyl 11,15-dihydroxy-9-oxo-15-methyl-13-thia-prostanoate, IR: 1,740, 3,420 cm$^{-1}$ NMR: 0.86; 1.21; 2.25; 3.61; 4.22; |
| 332 | Methyl 11,15-dihydroxy-9-oxo-13-thia-prostanoate, |
| 333 | Methyl 11,15-dihydroxy-9-oxo-15,16-dimethyl-13-thia-prostanoate, |
| 334 | Methyl 11,15-dihydroxy-9-oxo-17-ethyl-13-thia-prostanoate, |
| 335 | Methyl 11,15-dihydroxy-9-oxo-15-(4-tolyl)-13-thia-16,17,18,19,20-pentanor-prostanoate, |
| 336 | Methyl 11,15-dihydroxy-9-oxo-15-phenyl-13-thia-17,18,19,20-tetranor-prostanoate, |
| 337 | Methyl 11,15-dihydroxy-9-oxo-15-(4-fluorophenyl)-13-thia-17,18,19,20-tetranor-prostanoate, |
| 338 | Methyl 11,15-dihydroxy-9-oxo-15-(4-chlorophenyl)-13-thia-17,18,19,20-tetranor-prostanoate, |
| 339 | Methyl 11,15-dihydroxy-9-oxo-15-(4-tolyl)-13-thia-17,18,19,20-tetranor-prostanoate, |
| 340 | Methyl 11,15-dihydroxy-9-oxo-15-(3,4,5-trimethoxyphenyl)-13-thia-17,18,19,20-tetranor-prostanoate, |
| 341 | Methyl 11,15-dihydroxy-9-oxo-15-methyl-16-phenyl-13-thia-17,18,19,20-tetranor-prostanoate, |
| 342 | Methyl 11,15-dihydroxy-9-oxo-16-(3-chlorophenoxy)-13-thia-17,18,19,20-tetranor-prostanoate, |
| 343 | Methyl 11,15-dihydroxy-9-oxo-15-(2-naphthyl)-13-thia-17,18,19,20-tetranor-prostanoate, |
| 344 | Methyl 11,15-dihydroxy-9-oxo-15-(4-pyridyl)-13-thia-17,18,19,20-tetranor-prostanoate, IR: 1,600, 1,740, 3,000–3,500 cm$^{-1}$ NMR: 1.63; 2.28; 3.7; 4.29; 7.33; 8.45; |
| 345 | Methyl 11,15-dihydroxy-9-oxo-16-(3-chlorophenoxy)-13-thia-17,18,19,20-tetranor-5-prostenoate, |
| 346 | Methyl 11,15-dihydroxy-9-oxo-15-methyl-13-thia-5-prostenoate, IR: 1,710, 1,740, 2,900, 3,400 cm$^{-1}$ NMR: 1.27; 2.32; 3.7; 4.22; 5.43. |

EXAMPLE 347

A solution of 1 g of 9,11,15-trihydroxy-15-methyl-13-thia-prostanoic acid in 10 ml of ethanol is saturated with HCl at 0° C. The mixture is left to stand for 12 hours at 20° and filtered and the filtrate is evaporated. The residue is partitioned between methylene chloride and saturated sodium bicarbonate solution. The organic phase is separated off, dried over MgSO$_4$ and filtered, the solvent is stripped off and, after purification by chromatography, this gives ethyl 9,11,15-trihydroxy-15-methyl-13-thia-prostanoate.

Analogously to Example 347, the following compounds are obtainable by reaction with n-propanol, isopropanol, n-butanol or isobutanol:

| | |
|---|---|
| 348: | n-propyl 9,11,15-trihydroxy-15-methyl-13-thia-prostanoate, |
| 349: | isopropyl 9,11,15-trihydroxy-15-methyl-13-thia-prostanoate, |
| 350: | n-butyl 9,11,15-trihydroxy-15-methyl-13-thia-prostanoate, |
| 351: | isobutyl 9,11,15-trihydroxy-15-methyl-13-thia-prostanoate. |

EXAMPLE 352

A mixture of 1.24 g of 9α,11α,15-trihydroxy-16-(3-chlorophenoxy)-13-thia-17,18,19,20-tetranor-5-prostenoic acid, 0.46 ml of triethylamine and 40 ml of acetone is cooled to −20°, 0.432 ml of isobutyl chloroformate is added dropwise, the mixture is warmed to 25° after 5 minutes, 0.8 g of p-benzoylaminophenol, dissolved in 20 ml of dry pyridine, is added dropwise, the mixture is stirred for 2 hours at room temperature, the solvent is distilled off, the residue is taken up in ethyl acetate, the organic phase is washed with water and dried over Na$_2$SO$_4$, the solvent is distilled off and, after purification of the residue by chromatography (silica gel/ethyl acetate), this gives p-benzoylaminophenyl 9α,11α,-15-trihydroxy-16-(3-chlorophenoxy)-13-thia-17,18,19,20-tetranor-5-prostenoate.

Analogously to Example 352, the compounds of formula III mentioned in the following Examples 353 to 360 are obtainable by reacting the mixed anhydride prepared from 9α,11α,15-trihydroxy-16-(3-chlorophenoxy)-13-thia-17,18,19,20-tetranor-5-prostenoic acid and isobutyl formate, with the corresponding phenol of formula VI:

| Example | Compound of the formula III |
|---|---|
| 353 | p-Acetylamino-phenyl 9α,11α,15-trihydroxy-16-(3-chlorophenoxy)-13-thia-17,18,19,20-tetranor-5-prostenoate, |

| Example | Compound of the formula III |
|---|---|
| 354 | p-(p-Acetylamino-benzoylamino)-phenyl 9α,11α,15-trihydroxy-16-(3-chlorophenoxy)-13-thia-17,18,19,20-tetranor-5-prostenoate, |
| 355 | p-(p-Benzoyl-amino-benzoylamino)-phenyl-9α,11α,15-trihydroxy-16-(3-chlorophenoxy)-13-thia-17,18,19,20-tetranor-5-prostenoate, |
| 356 | p-Ureidophenyl 9α,11α,15-trihydroxy-16-(3-chlorophenoxy)-13-thia-17,18,19,20-tetranor-5-prostenoate, |
| 357 | p-(3-Phenyl-ureido)-phenyl 9α,11α,15-trihydroxy-16-(3-chlorophenoxy)-13-thia-17,18,19,20-tetranor-5-prostenoate, |
| 358 | 4-Acetylamino-1-naphthyl 9α,11α,15-trihydroxy-16-(3-chlorophenoxy)-13-thia-17,18,19,20-tetranor-5-prostenoate, |
| 359 | 4-Benzoylamino-1-naphthyl 9α,11α,15-trihydroxy-16-(3-chlorophenoxy)-13-thia-17,18,19,20-tetranor-5-prostenoate, |
| 360 | 4-Ureido-1-naphthyl 9α,11α,15-trihydroxy-16-(3-chlorophenoxy)-13-thia-17,18,19,20-tetranor-5-prostenoate. |

EXAMPLE 361

Analogously to Example 352, benzoylaminophenyl 11α,15-dihydroxy-9-oxo-15-methyl-13-thia-prostanoate, m.p.=74°–76° C. (from diethyl ether), is obtained from 11α-15-dihydroxy-9-oxo-15-methyl-13-thia-prostanoic acid by reaction with benzoylaminophenol.

EXAMPLE 362

0.1 g of methyl 9,11,15-trihydroxy-16-(3-chlorophenoxy)-13-thia-17,18,19,20-tetranor-5-prostenoate is stirred for 90 hours in a mixture of 2 ml of a saturated aqueous NaCN solution and 6 ml of methanol. The reaction mixture is saturated with NaCl and extracted with chloroform, the organic phase is washed with water and dried over $MgSO_4$, the solvent is distilled off and, after purification of the residue by chromatography on silica gel, this gives 9,11,15-trihydroxy-16-(3-chlorophenoxy)-13-thia-17,18,19,20-tetranor-4-prostenoic acid.

IR: 1,710, 2,400, 3,650 cm$^{-1}$.
NMR: 1.1–2.6; 2.6–3.1; 4.05; 4.2; 5.3; 5.4; 6.6–7.4.

EXAMPLE 363

4.5 g of 9,11,15-trihydroxy-16-(3-chlorophenoxy)-13-thia-17,18,19,20-tetranor-5-prostenoic acid, dissolved in 20 ml of dry diethyl ether, is added dropwise to an ethanolic sodium ethanolate solution prepared from 0.24 g of sodium and 20 ml of dry ethanol, the solvent is distilled off and the sodium salt of 9,11,15-trihydroxy-16-(3-chlorophenoxy)-13-thia-17,18,19,20-tetranor-5-prostenoic acid is obtained as the residue.

EXAMPLE 364

Analogously to Example 363, the calcium salt of 9,11,15-trihydroxy-16-(3-chlorophenoxy)-13-thia-17,18,19,20-tetranor-5-prostenoic acid is obtained using an ethanolic calcium ethanolate solution prepared from 0.40 g of calcium and 20 ml of dry ethanol.

The following examples relate to mixtures of compounds of formula III with excipients or auxiliaries which are customary in pharmacy, which mixtures can be used, in particular, as medicaments:

EXAMPLE A - Tablets

A mixture consisting of 30 g of p-benzoylaminophenyl 11α,15-dihydroxy-15-methyl-9-oxo-13-thiaprostanoate, 50 g of lactose, 16 g of maize starch, 2 g of cellulose powder and 2 g of magnesium stearate is compressed in the conventional manner to form tablets, so that each tablet contains 10 mg of the active ingredient.

EXAMPLE B - Coated Tablets

Analogously to Example A, tablets are formed by compression and are then covered in the conventional manner with a coating consisting of sugar, maize starch, talc and tragacanth.

EXAMPLE C - Injection Solution 10 g of 9α,11α,15-trihydroxy-16-(3-chlorophenoxy)13-thia-17,18,19,20-tetranor-5-prostenoic acid is dissolved in a mixture of 4 liters of distilled water, 0.5 liter of ethanol and 0.5 liter of propylene glycol and the solution is filtered under sterile conditions. The resulting injection solution is filled, as required, into ampoules containing 2.5 ml, 5 ml or 10 ml of the injection solution.

Tablets, coated tablets and injection solutions which contain one or more of the other active ingredients of formula III are obtainable analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

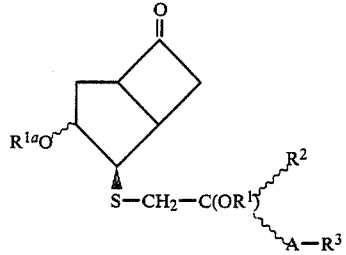

wherein A is a C—C single bond, —$CH_2$—, —CH(CH$_3$)—, —C(CH$_3$)$_2$—, —$CH_2$—$CH_2$—, —CH(CH$_3$)CH$_2$—, —C(CH$_3$)$_2$CH$_2$—, —$CH_2$—$CH_2$—$CH_2$— or —$CH_2$O—; $R^{1a}$ and $R^1$ each independently is hydrogen or a protective group which can be cleaved by solvolysis with an acid or a base or by catalytic hydrogenolysis; $R^2$ is H or alkyl of 1 to 3 C atoms; $R^3$ is alkyl of 3 to 5 C atoms, phenyl or phenyl which is monosubstituted to trisubstituted by F, Cl, OH, OCH$_3$, OC$_2$H$_5$, CF$_3$ or alkyl or 1 to 3 C atoms, or, when A is not —$CH_2$O—, can also be pyridyl, thienyl, naphthyl or alkoxy of 1 to 4 C atoms; ◂ indicates a bond in the β-position and a wavy line (⁓) means that the bond can be in the α- or β-position.

2. A compound of claim 1 wherein A=—$CH_2$—, —CH(CH$_3$)— or —C(CH$_3$)$_2$— and $R^3$=butyl.

3. A compound of claim 1 wherein A=—$CH_2$—, —CH(CH$_3$)— or —C(CH$_3$)$_2$—, $R^2$=methyl and $R^3$=butyl.

4. A compound of claim 1 wherein A =—CH₂—CH₂ or —CH₂O— and R³=phenyl, 3-chlorophenyl, 3-trifluoromethylphenyl or 3-methoxyphenyl.

5. A compound of claim 1 wherein A=—CH₂—CH₂— or —CH₂O—, R²=H or methyl and R³=phenyl, 3-chlorophenyl, 3-trifluoromethylphenyl or 3-methoxyphenyl.

6. A compound of claim 1 wherein A=—CH₂—CH₂— or —CH₂O—, R¹=H, R²=H or methyl and R³=phenyl, 3-chlorophenyl, 3-trifluoromethylphenyl or 3-methoxyphenyl.

7. 3α-Hydroxy-2β-(3-(3-chlorophenoxy)-2-hydroxypropylthio)-1βH,5βH-bicyclo[3.2.0]heptan-6-one, a compound of claim 1.

8. 3α-Hydyroxy-2β-(2-hydroxy-2-methyl-heptylthio)bicyclo[3.2.0]heptan-6-one, a compound of claim 1.

9. A compound of claim 1 wherein R² is H.

10. A compound of claim 1 wherein R² is alkyl.

11. A compound of claim 1 wherein A is —CH₂O—.

12. A compound of claim 1 wherein R³ is alkyl.

13. A compound of claim 1 wherein R³ is pyridyl, thienyl, or naphthyl.

14. A compound of claim 1 wherein R³ is phenyl or substituted phenyl.

15. A process for preparing a compound regiospecifically in the 2β-position, the compound being of the formula

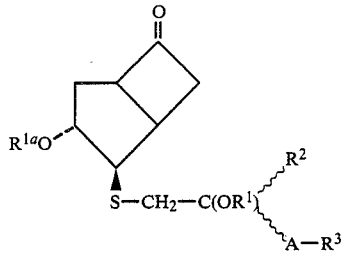

wherein A is a C—C single bond, —CH₂, —CH(CH₃)—, —C(CH₃)₂—, —CH₂—CH₂—, —CH(CH₃)CH₂—, —C(CH₃)₂CH₂—, —CH₂—CH₂—CH₂— or —CH₂O—; R¹ᵃ and R¹ each independently is hydrogen or a protective group which can be cleaved by solvolysis with an acid or a base or by catalytic hydrogenolysis; R² is H or alkyl of 1 to 3 C atoms; R³ is alkyl of 3 to 5 C atoms, phenyl or phenyl which is monosubstituted to trisubstituted by F, Cl, OH, OCH₃, OC₂H₅, CF₃ or alkyl of 1 to 3 C atoms, or, when A is not —CH₂O—, can also be pyridyl, thienyl, naphthyl or alkoxy of 1 to 4 C atoms; ----indicates a bond in the α-position,— indicates a bond in the β-position and a wavy line means that the bond can be in the α-or β-position
comprising reacting, under basic conditions the corresponding 2 β-bromo-3α-hydroxy-bicyclo [3.2.0]heptan-6-one, with retention of configuration, at the 2- and 3-positions,
with a thiol or thiolate of the formula

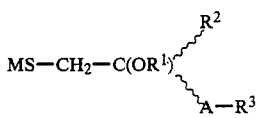

wherein M is H, one equivalent of a metal atom or an ammonium ion and A and R¹ to R³ are as defined above.

16. A process of claim 15 wherein said heptanone reactant has the configuration 2β, 3α-.

17. A process of claim 15 further comprising blocking one or more hydroxy groups on the product of said reaction by a protective group which can be cleaved by solvolysis with an acid or a base or by catalytic hydrogenolysis.

* * * * *